United States Patent
Czapar et al.

(10) Patent No.: US 11,930,857 B2
(45) Date of Patent: Mar. 19, 2024

(54) TEMPERATURE ADJUSTMENT OF A VAPORIZER DEVICE

(71) Applicant: JUUL Labs, Inc., San Francisco, CA (US)

(72) Inventors: Matthew Czapar, San Francisco, CA (US); Christopher Loental, San Francisco, CA (US); Katherine Murphy, San Francisco, CA (US); Oliver Farshi, Oakland, CA (US)

(73) Assignee: Pax Labs, Inc., San Francisco, CA (US)

( * ) Notice: Subject to any disclaimer, the term of this patent is extended or adjusted under 35 U.S.C. 154(b) by 0 days.

(21) Appl. No.: 16/926,439

(22) Filed: Jul. 10, 2020

(65) Prior Publication Data

US 2021/0007407 A1  Jan. 14, 2021

Related U.S. Application Data

(60) Provisional application No. 62/873,588, filed on Jul. 12, 2019.

(51) Int. Cl.
*A24F 40/57* (2020.01)
*A24F 40/53* (2020.01)
*A24F 40/60* (2020.01)
*A24F 40/65* (2020.01)
*A61M 11/04* (2006.01)
*A61M 15/06* (2006.01)
*H05B 1/02* (2006.01)

(52) U.S. Cl.
CPC ............ *A24F 40/57* (2020.01); *A24F 40/53* (2020.01); *A24F 40/60* (2020.01); *A24F 40/65* (2020.01); *A61M 11/042* (2014.02); *A61M 15/06* (2013.01); *H05B 1/0297* (2013.01); *A61M 2205/14* (2013.01); *A61M 2205/3372* (2013.01); *A61M 2205/50* (2013.01); *A61M 2205/502* (2013.01); *A61M 2205/52* (2013.01); *A61M 2205/587* (2013.01)

(58) Field of Classification Search
CPC .......... A61M 15/06; A24F 40/57; A24F 40/60
See application file for complete search history.

(56) References Cited

U.S. PATENT DOCUMENTS

2018/0077967 A1   3/2018   Hatton et al.

FOREIGN PATENT DOCUMENTS

WO   WO-2019104227 A1   5/2019

*Primary Examiner* — Anthony Calandra
(74) *Attorney, Agent, or Firm* — Mintz Levin Cohn Ferris Glovsky and Popeo, P.C.

(57) ABSTRACT

Features relating to vaporizer devices configured to allow for temperature adjustment are provided. User controlled actions with respect to removing a cartridge from a vaporizer body and inserting the cartridge into the vaporizer body provide for temperature adjustment, where the temperature refers to a setpoint temperature of operation of the vaporizer device. The temperature adjustment aspects of the current subject matter provide a user with a controlled, intuitive, and simple method to adjust the setpoint temperature of the vaporizer device by incrementing through a sequence of setpoint temperatures.

28 Claims, 12 Drawing Sheets

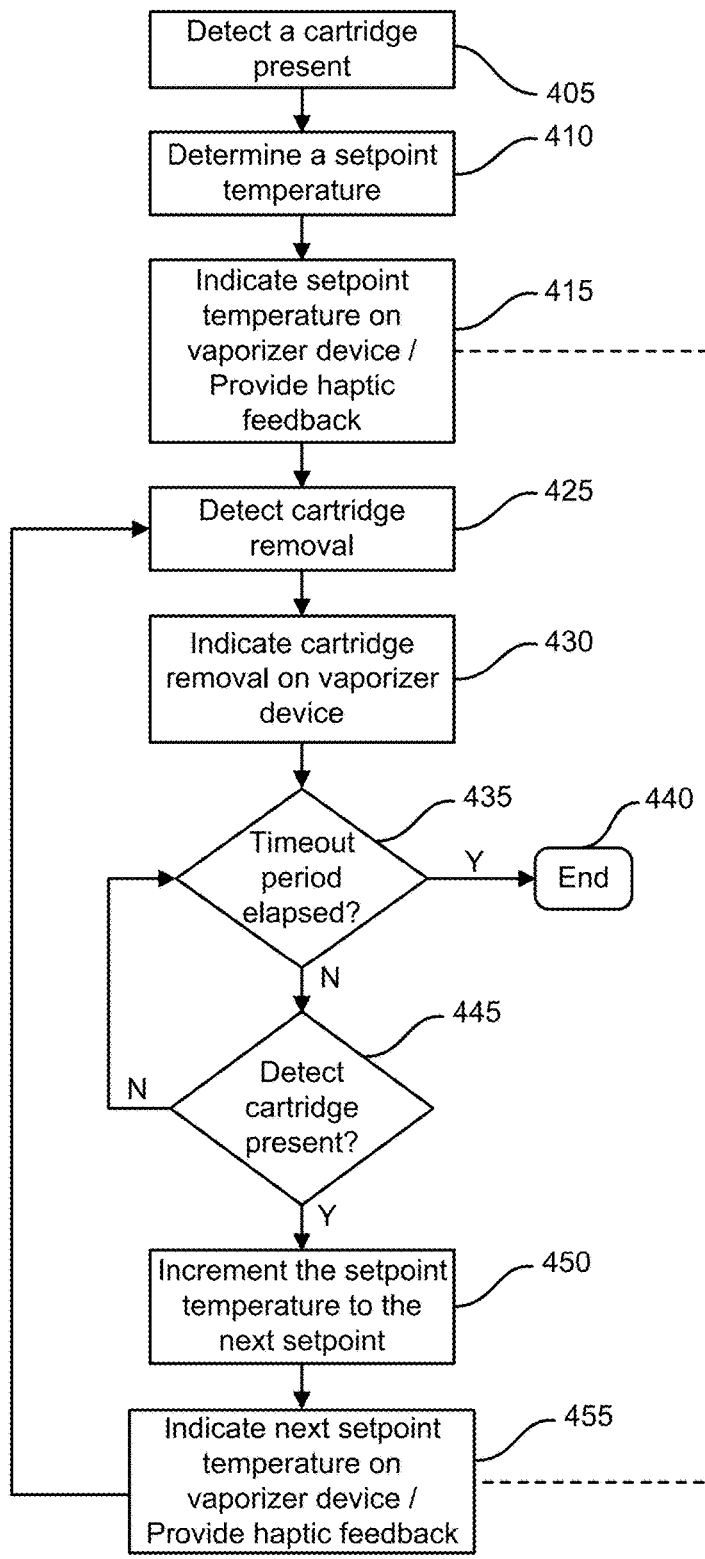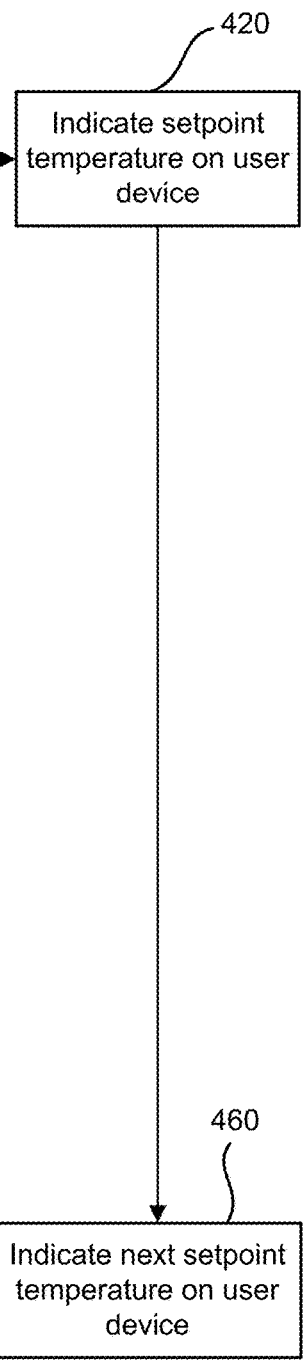
FIG. 4

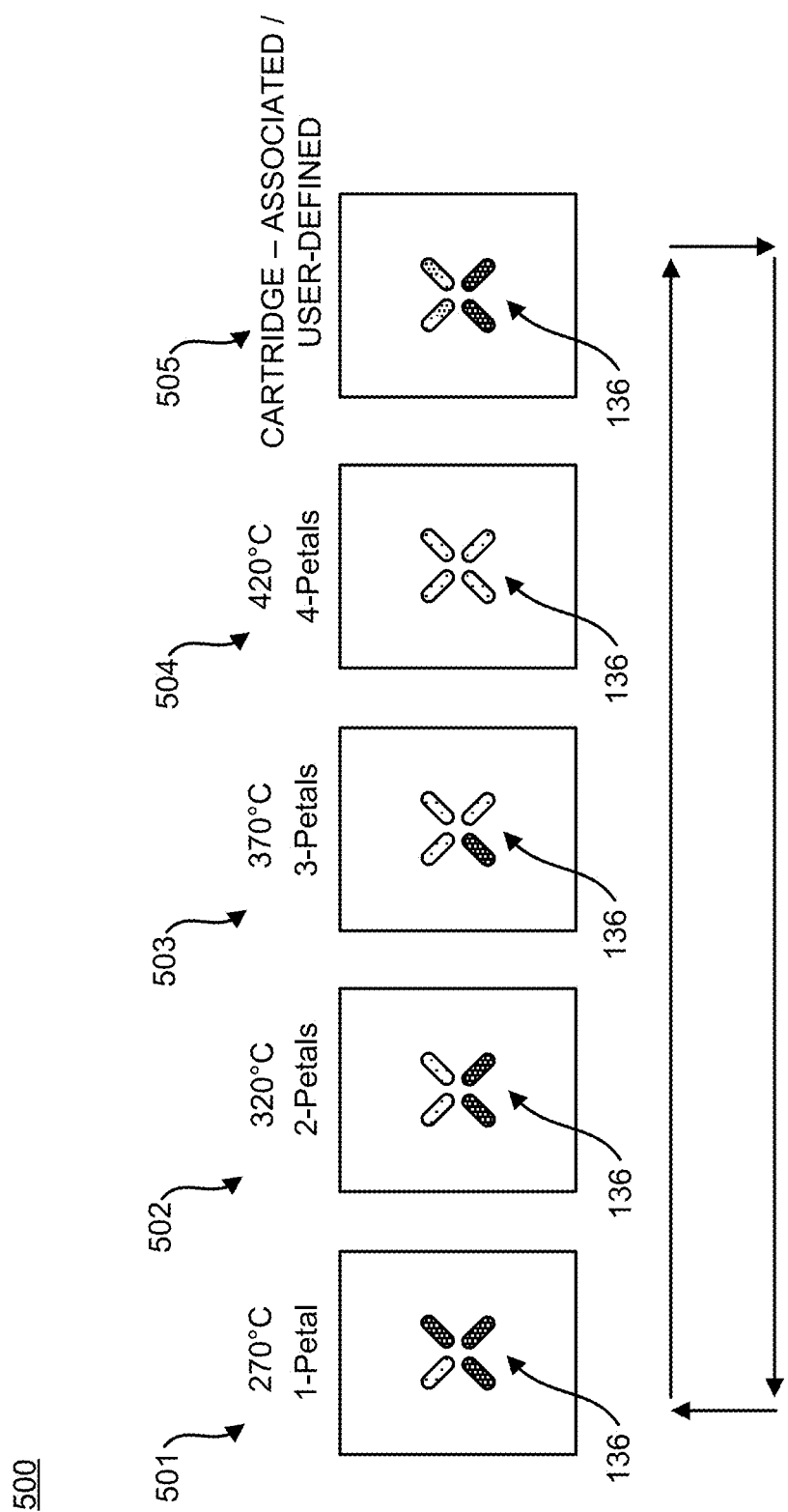

TEMPERATURE ADJUSTMENT OF A VAPORIZER DEVICE

CROSS-REFERENCE TO RELATED APPLICATIONS

This application claims priority to U.S. Provisional Patent Application No. 62/873,588, filed Jul. 12, 2019 and entitled "Temperature Adjustment of a Vaporizer Device," the content of which is incorporated in its entirety by reference herein.

TECHNICAL FIELD

The current subject matter described herein relates generally to vaporizer devices, such as portable, personal vaporizer devices for generating and delivering an inhalable aerosol from one or more vaporizable materials, and more particularly relates to temperature adjustment of vaporizer devices.

BACKGROUND

Vaporizing devices, including electronic vaporizers or e-vaporizer devices, allow the delivery of vapor and aerosol containing one or more active ingredients by inhalation of the vapor and aerosol. Electronic vaporizer devices are gaining increasing popularity both for prescriptive medical use, in delivering medicaments, and for consumption of nicotine, tobacco, other liquid-based substances, and other plant-based smokeable materials, such as cannabis, including solid (e.g., loose-leaf or flower) materials, solid/liquid (e.g., suspensions, liquid-coated) materials, wax extracts, and prefilled pods (cartridges, wrapped containers, etc.) of such materials. Electronic vaporizer devices in particular may be portable, self-contained, and convenient for use.

SUMMARY

Aspects of the current subject matter relate to temperature adjustment of a vaporizer device. In particular, in accordance with implementations of the current subject matter, user controlled actions with respect to cartridge removal from and insertion into a cartridge receptacle of a vaporizer body serve to adjust a temperature of the vaporizer device.

According to an aspect of the current subject matter, a method includes detecting insertion of a cartridge in a vaporizer body, the cartridge including a heating element configured to deliver heat to a vaporizable material contained in the cartridge, where the heat causes vaporization of the vaporizable material; determining, in response to detecting insertion of the cartridge, a setpoint temperature for the heating element; providing, on a display of the vaporizer body, an indication of the setpoint temperature; detecting removal of the cartridge from the vaporizer body; providing, on the display of the vaporizer body and in response to detecting removal of the cartridge, an indication of the removal of the cartridge; detecting, during a timeout period and following removal of the cartridge, reinsertion of the cartridge in the vaporizer body; incrementing, in response to detecting reinsertion of the cartridge during the timeout period, the setpoint temperature to a next setpoint temperature in a sequence of setpoint temperatures; providing, on the display of the vaporizer body, an indication of the next setpoint temperature; and activating the heating element to reach the next setpoint temperature for vaporization of the vaporizable material.

According to an inter-related aspect, a vaporizer device includes at least one data processor and at least one memory storing instructions which, when executed by the at least one data processor, cause operations including detecting insertion of a cartridge in a vaporizer body, the cartridge including a heating element configured to deliver heat to a vaporizable material contained in the cartridge, where the heat causes vaporization of the vaporizable material; determining, in response to detecting insertion of the cartridge, a setpoint temperature for the heating element; providing, on a display of the vaporizer body, an indication of the setpoint temperature; detecting removal of the cartridge from the vaporizer body; providing, on the display of the vaporizer body and in response to detecting removal of the cartridge, an indication of the removal of the cartridge; detecting, during a timeout period and following removal of the cartridge, reinsertion of the cartridge in the vaporizer body; incrementing, in response to detecting reinsertion of the cartridge during the timeout period, the setpoint temperature to a next setpoint temperature in a sequence of setpoint temperatures; providing, on the display of the vaporizer body, an indication of the next setpoint temperature; and activating the heating element to reach the next setpoint temperature for vaporization of the vaporizable material.

According to an inter-related aspect, a non-transitory computer readable medium is provided, the non-transitory computer readable medium storing instructions, which when executed by at least one data processor, result in operations including detecting insertion of a cartridge in a vaporizer body, the cartridge including a heating element configured to deliver heat to a vaporizable material contained in the cartridge, where the heat causes vaporization of the vaporizable material; determining, in response to detecting insertion of the cartridge, a setpoint temperature for the heating element; providing, on a display of the vaporizer body, an indication of the setpoint temperature; detecting removal of the cartridge from the vaporizer body; providing, on the display of the vaporizer body and in response to detecting removal of the cartridge, an indication of the removal of the cartridge; detecting, during a timeout period and following removal of the cartridge, reinsertion of the cartridge in the vaporizer body; incrementing, in response to detecting reinsertion of the cartridge during the timeout period, the setpoint temperature to a next setpoint temperature in a sequence of setpoint temperatures; providing, on the display of the vaporizer body, an indication of the next setpoint temperature; and activating the heating element to reach the next setpoint temperature for vaporization of the vaporizable material.

In some variations, one or more of the features disclosed herein including the following features can optionally be included in any feasible combination. The setpoint temperature may include a default setpoint temperature, a cartridge-associated setpoint temperature, a vaporizer body-associated setpoint temperature, a previous setpoint temperature, or a user-defined setpoint temperature. Determining the setpoint temperature may include at least one of accessing data stored on a data tag of the cartridge, accessing a memory component in the vaporizer body, and receiving the setpoint temperature from a device in communication with the vaporizer body. The display may include a plurality of light-emitting diodes, where the indication of the setpoint temperature may include a first predefined pattern of illumination of the plurality of light-emitting diodes, where the indication of the next setpoint temperature may include a second predefined pattern of illumination of the plurality of light-emitting diodes. The display may include a plurality of light-emitting diodes, where the indication of the removal of the cartridge may include the plurality of light-emitting diodes illuminated in a predefined cartridge removal pattern. A length of time of the predefined cartridge removal pattern may equal the timeout period. The indication of the next setpoint temperature may interrupt the indication of the removal of the cartridge. The sequence of setpoint temperatures may define a series of temperatures including at least the setpoint temperature and the next setpoint temperature. The sequence of setpoint temperatures may further include at least one of a cartridge-associated setpoint temperature and a user-defined setpoint temperature. The at least one of the cartridge-associated setpoint temperature and the user-defined setpoint temperature may be positioned within the sequence of setpoint temperatures based on at least one of a value of the cartridge-associated setpoint temperature and a value of the user-defined setpoint temperature, or may be positioned as a last setpoint temperature within the sequence of setpoint temperatures. In response to detecting insertion of the cartridge, an indication of the insertion of the cartridge may be provided on the display of the vaporizer body, where the indication of the insertion of cartridge precedes the indication of the setpoint temperature. A second removal of the cartridge from the vaporizer body may be detected; in response to detecting the second removal of the cartridge, an indication of the second removal of the cartridge may be provided on the display of the vaporizer body; during a second timeout period and following the second removal of the cartridge, reinsertion of the cartridge in the vaporizer body may be detected; in response to detecting reinsertion of the cartridge during the second timeout period, the next setpoint temperature may be incremented to a third setpoint temperature in the sequence of setpoint temperatures; an indication of the third setpoint temperature may be provided on the display of the vaporizer body; and the heating element may be activated to reach the third setpoint temperature for vaporization of the vaporizable material.

The details of one or more variations of the subject matter described herein are set forth in the accompanying drawings and the description below. Other features and advantages of the subject matter described herein will be apparent from the description and drawings, and from the claims. The claims that follow this disclosure are intended to define the scope of the protected subject matter.

DESCRIPTION OF THE DRAWINGS

The accompanying drawings, which are incorporated in and constitute a part of this specification, show certain aspects of the subject matter disclosed herein and, together with the description, help explain some of the principles associated with the disclosed implementations. In the drawings.

FIG. 4 shows a process flow chart illustrating features of a method consistent with some implementations of the current subject matter;

FIG. 5A-FIG. 5F are example representations of temperature adjustment features consistent with implementations of the current subject matter.

When practical, similar reference numbers denote similar structures, features, or elements.

DETAILED DESCRIPTION

Figure 1A:
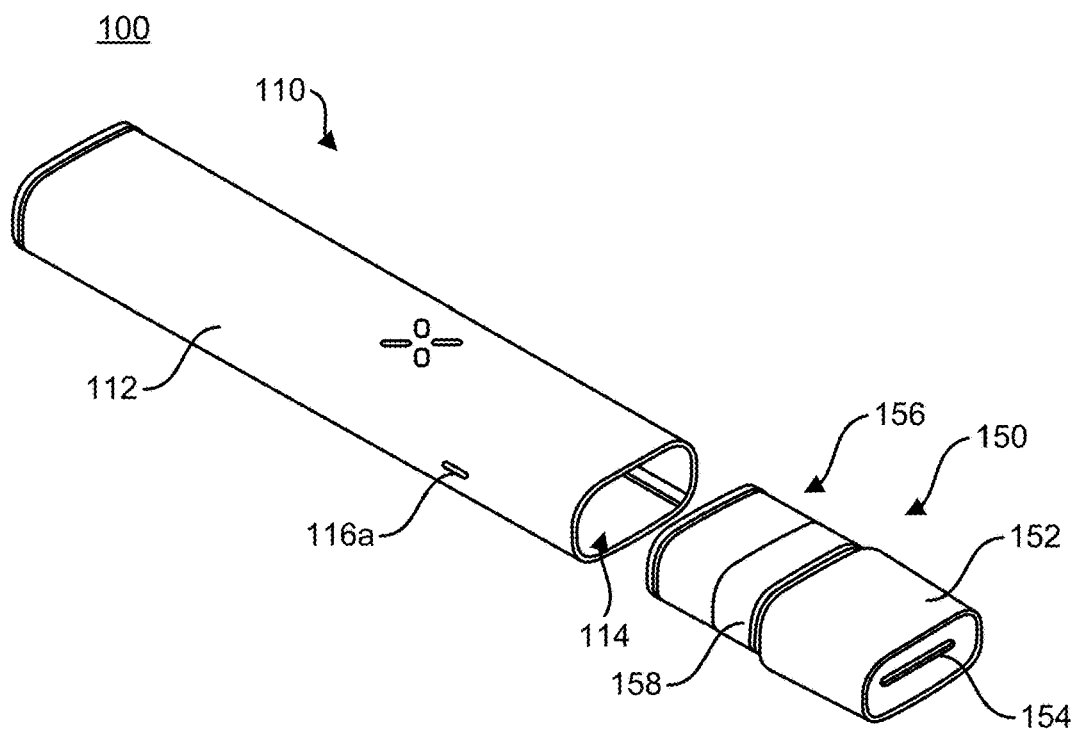
FIG. 1A-FIG. 1F illustrate features of a vaporizer device including a vaporizer body and a cartridge consistent with implementations of the current subject matter.

Aspects of the current subject matter relate to temperature adjustment of a vaporizer device and more particularly to user controlled actions to adjust a setpoint temperature of operation of a vaporizer device.

In particular, in accordance with implementations of the current subject matter, user controlled actions with respect to cartridge removal from and insertion into a cartridge receptacle of a vaporizer body provide for temperature adjustment, where the temperature refers to a setpoint temperature of operation of the vaporizer device (e.g., the temperature at which a heating element operates to vaporize vaporizable material contained in the cartridge). The setpoint temperature affects the strength of vapor being produced by the vaporizer device. For example, higher temperatures may produce a denser vapor (e.g., a greater mass of aerosol or greater total particulate matter) compared to vapor produced from a lower temperature. Users may have preferences with respect to the setpoint temperature and may wish to adjust the setpoint temperature. For example, a user may at times prefer a denser vapor and thus a higher temperature, while at other times may prefer a less dense vapor and thus a lower temperature. A user may also wish to explore a range of setpoint temperatures. Additionally, the type of vaporizable material is also a factor with respect to the setpoint temperature. For example, a lower setpoint temperature may be suitable or preferable for a first type of vaporizable material, while a higher setpoint temperature may be suitable or preferable for a second type of vaporizable material.

The temperature adjustment aspects of the current subject matter provide a user a controlled, intuitive, and simple method to adjust the setpoint temperature of the vaporizer device. Moreover, the temperature adjustment aspects provide for quickly incrementing through a sequence of setpoint temperatures, allowing the user to select the desired setpoint temperature for use with the vaporizer device. Significantly, the temperature adjustment aspects of the current subject matter do not require use of a mobile or web-based application on a user device, nor do they require an accelerometer, which may typically be utilized for user-controlled actions with respect to operational adjustments of a vaporizer device.

Before providing additional details regarding aspects of temperature adjustment of a vaporizer device, the following provides a description of some examples of vaporizer devices including a vaporizer body and a cartridge in which aspects of the current subject matter may be implemented. The following descriptions are meant to be exemplary, and aspects related to temperature adjustment consistent with the current subject matter are not limited to the example vaporizer devices described herein.

Implementations of the current subject matter include devices relating to vaporizing of one or more materials for inhalation by a user. The term "vaporizer" may be used generically in the following description and may refer to a vaporizer device, such as an electronic vaporizer. Vaporizers consistent with the current subject matter may be referred to by various terms such as inhalable aerosol devices, aerosolizers, vaporization devices, electronic vaping devices, electronic vaporizers, vape pens, etc. Examples of vaporizers consistent with implementations of the current subject matter include electronic vaporizers, electronic cigarettes, e-cigarettes, or the like. In general, such vaporizers are often portable, hand-held devices that heat a vaporizable material to provide an inhalable dose of the material. The vaporizer may include a heater configured to heat a vaporizable material which results in the production of one or more gas-phase components of the vaporizable material. A vaporizable material may include liquid and/or oil-type plant materials, or a semi-solid like a wax, or plant material such as leaves or flowers, either raw or processed. The gas-phase components of the vaporizable material may condense after being vaporized such that an aerosol is formed in a flowing air stream that is deliverable for inhalation by a user. The vaporizers may, in some implementations of the current subject matter, be particularly adapted for use with an oil-based vaporizable material, such as cannabis-derived oils although other types of vaporizable materials may be used as well.

One or more features of the current subject matter, including one or more of a cartridge (also referred to as a vaporizer cartridge or pod) and a reusable vaporizer device body (also referred to as a vaporizer device base, a body, a vaporizer body, or a base), may be employed with a suitable vaporizable material (where suitable refers in this context to being usable with a device whose properties, settings, etc. are configured or configurable to be compatible for use with the vaporizable material). The vaporizable material may include one or more liquids, such as oils, extracts, aqueous or other solutions, etc., of one or more substances that may be desirably provided in the form of an inhalable aerosol. The cartridge may be inserted into the vaporizer body, and then the vaporizable material heated which results in the inhalable aerosol.

Figure 1B:
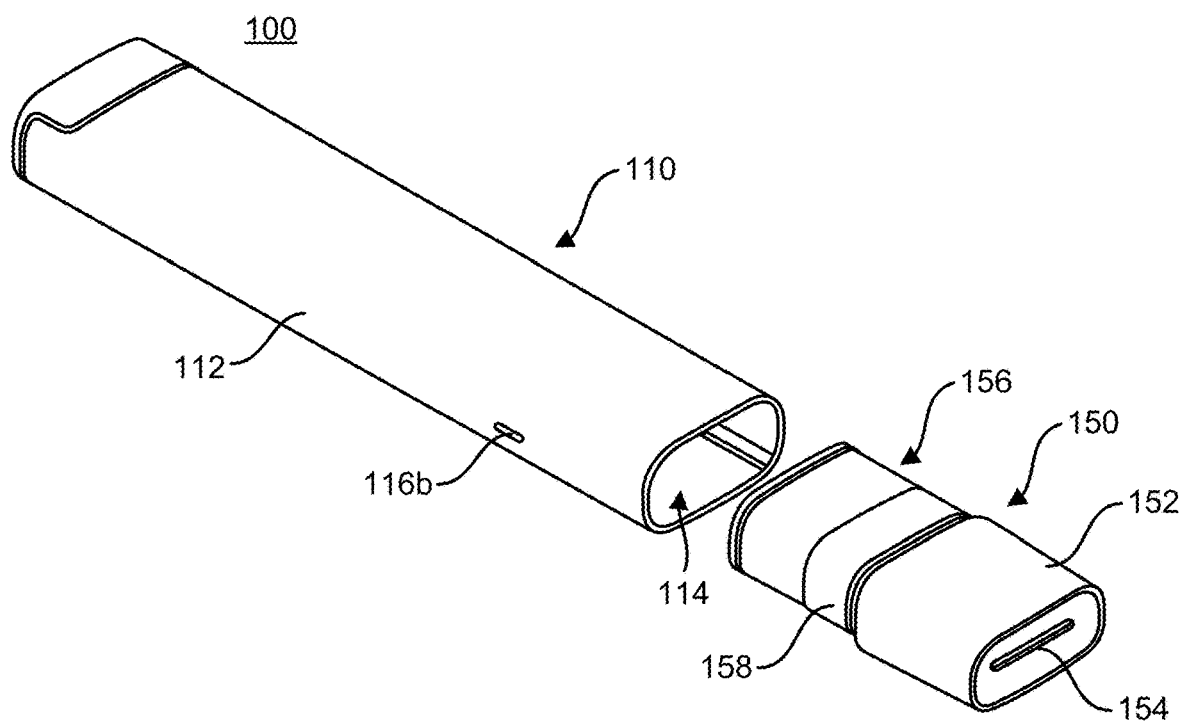
Figure 1C:
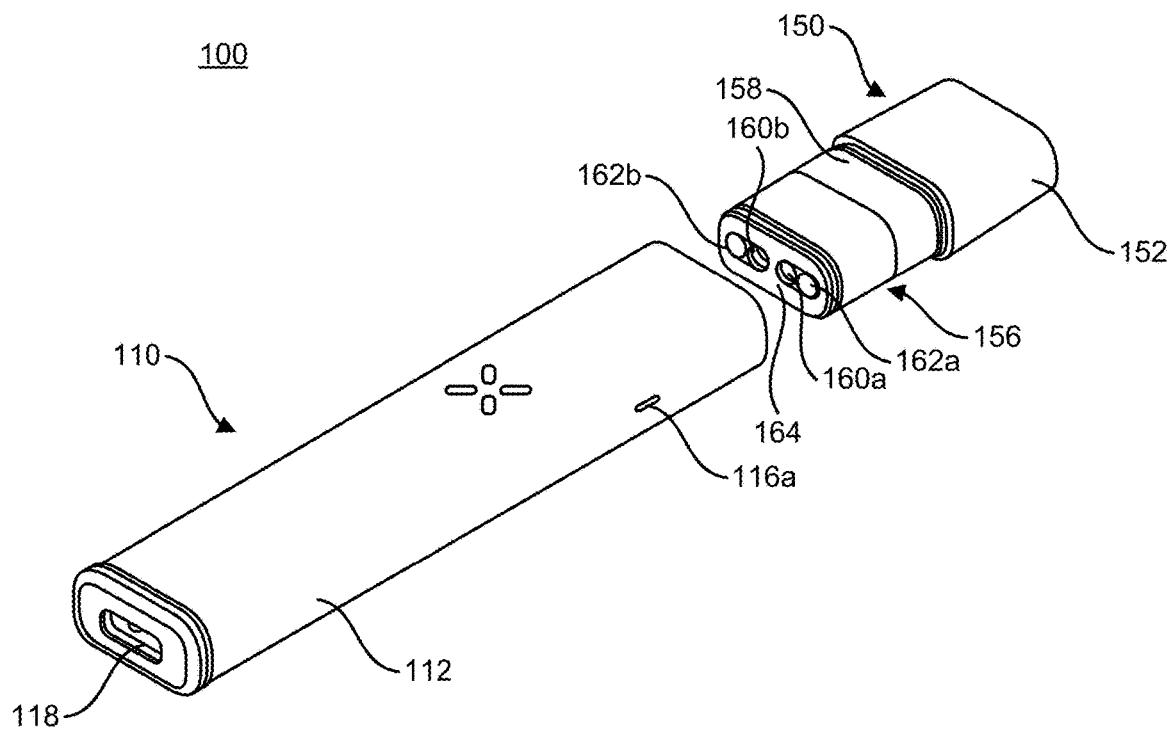
Figure 1D:
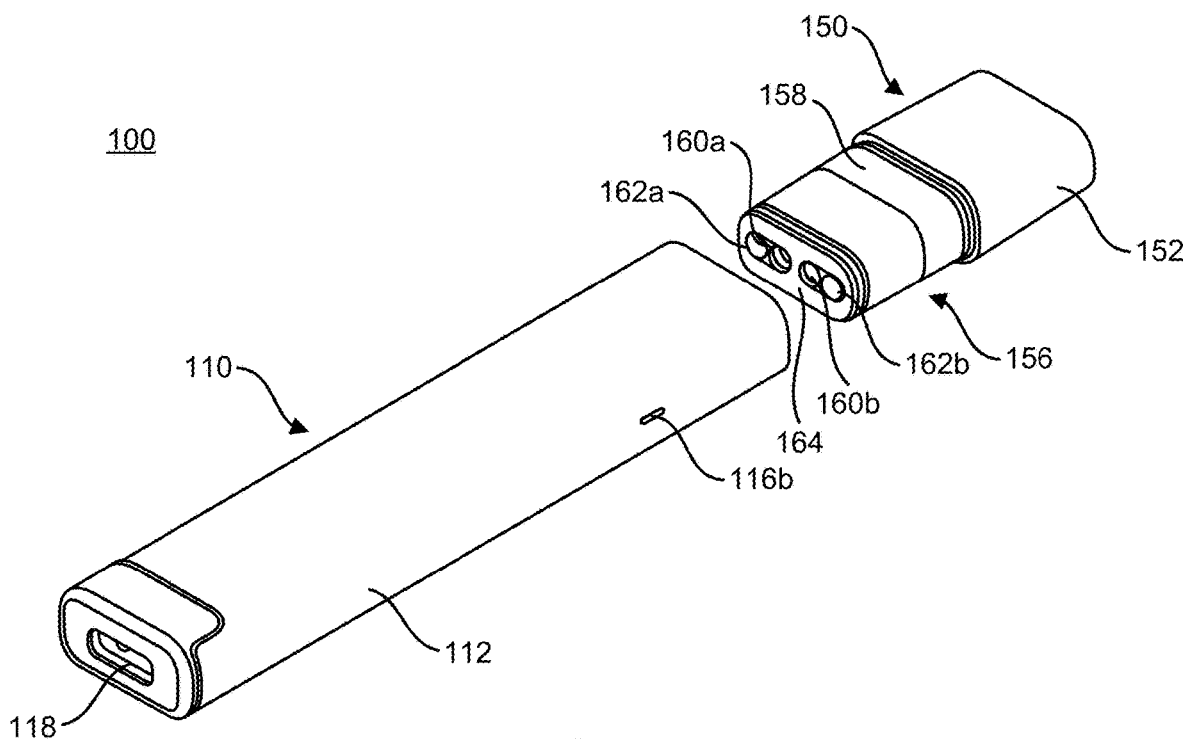
Figure 1E:
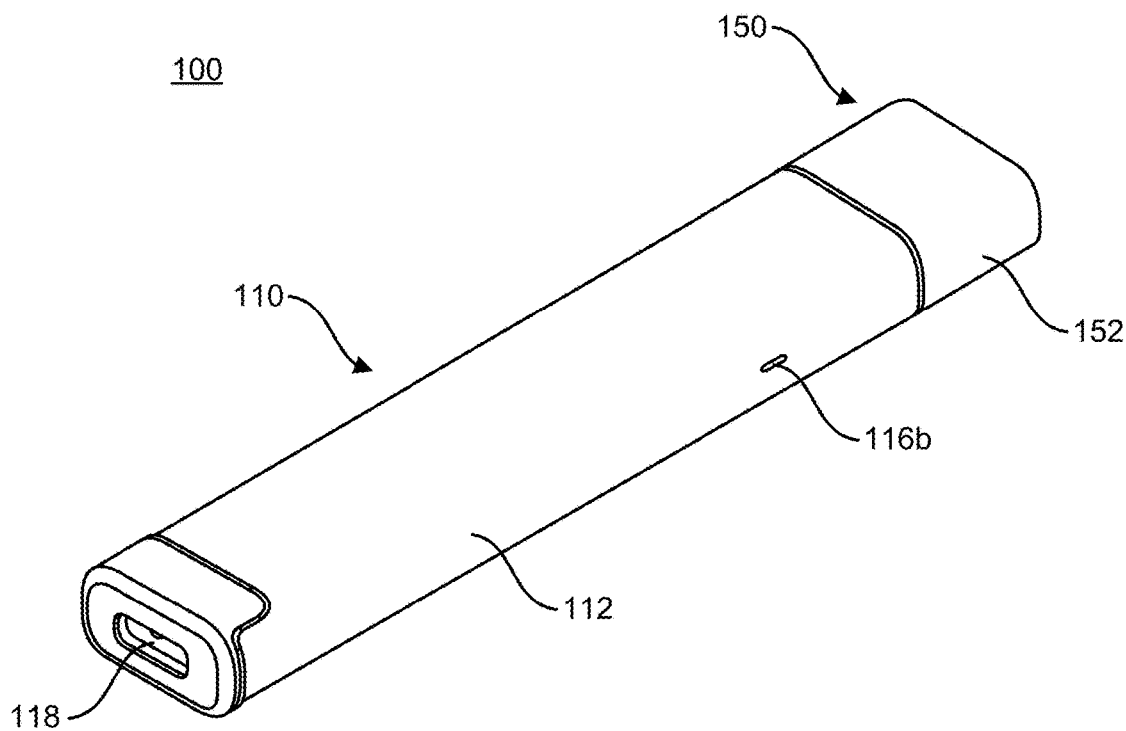
Figure 1F:
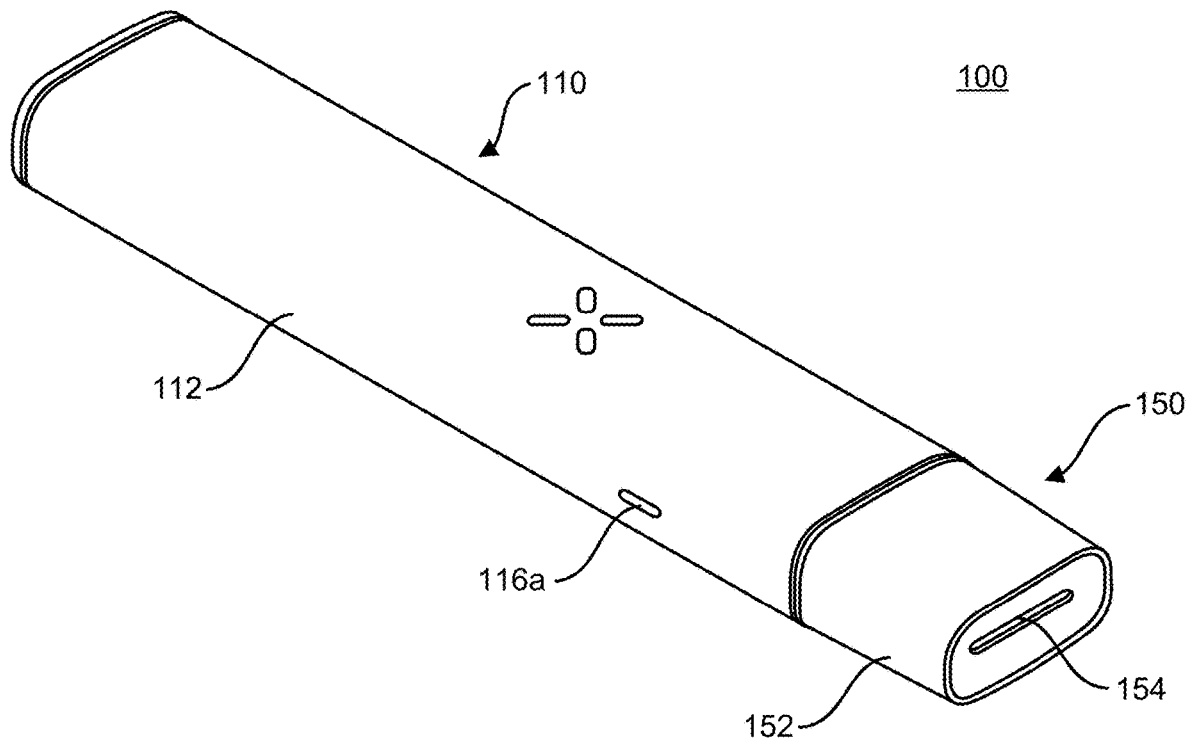

FIG. 1A-FIG. 1F illustrates features of a vaporizer device 100 including a vaporizer body 110 and a cartridge 150 consistent with implementations of the current subject matter. FIG. 1A is a bottom perspective view, and FIG. 1B is a top perspective view of the vaporizer device 100 with the cartridge 150 separated from a cartridge receptacle 114 on the vaporizer body 110. Both of the views in FIG. 1A and FIG. 1B are shown looking towards a mouthpiece 152 of the cartridge 150. FIG. 1C is a bottom perspective view, and FIG. 1D is a top perspective view of the vaporizer device with the cartridge 150 separated from the cartridge receptacle 114 of the vaporizer body 110. FIG. 1C and FIG. 1D are shown looking toward the distal end of the vaporizer body 110. FIG. 1E is top perspective view, and FIG. 1F is a bottom perspective view of the vaporizer device 100 with the cartridge 150 engaged for use with the vaporizer body 110.

As shown in FIG. 1A-FIG. 1D, the cartridge 150 includes, at the proximal end, a mouthpiece 152 that is attached over a cartridge body 156 that forms a reservoir or tank 158 that holds a vaporizable material. The cartridge body 156 may be transparent, translucent, opaque, or a combination thereof. The mouthpiece 152 may include one or more openings 154 (see FIG. 1A, FIG. 1B, FIG. 1F) at the proximal end out of which vapor may be inhaled, by drawing breath through the vaporizer device 100. The distal end of the cartridge body 156 may couple to and be secured to the vaporizer body 110 within the cartridge receptacle 114 of the vaporizer body 110. Power pin receptacles 160a,b (see FIG. 1C, FIG. 1D) of the cartridge 150 mate with respective power pins or contacts 122a,b (see, for example, FIG. 2) of the vaporizer body 110 that extend into the cartridge receptacle 114. The cartridge 150 also includes air flow inlets 162a,b on the distal end of the cartridge body 156.

A tag 164, such as a data tag, a near-field communication (NFC) tag, or other type of wireless transceiver or communication tag, may be positioned on at least a portion of the distal end of the cartridge body 156. As shown in FIG. 1C and FIG. 1D, the tag 164 may substantially surround the power pin receptacles 160a,b and the air flow inlets 162a,b, although other configurations of the tag 164 may be implemented as well. For example, the tag 164 may be positioned between the power pin receptacle 160a and the power pin receptacle 160b, or the tag 164 may be shaped as a circle, partial circle, oval, partial oval, or any polygonal shape encircling or partially encircling the power pin receptacles 160a,b and the air flow inlets 162a,b or a portion thereof.

In the example of FIG. 1A, the vaporizer body 110 has an outer shell or cover 112 that may be made of various types of materials, including for example aluminum (e.g., AL6063), stainless steel, glass, ceramic, titanium, plastic (e.g., Acrylonitrile Butadiene Styrene (ABS), Nylon, Polycarbonate (PC), Polyethersulfone (PESU), and the like), fiberglass, carbon fiber, and any hard, durable material. The proximal end of the vaporizer body 110 includes an opening forming the cartridge receptacle 114, and the distal end of the vaporizer body 110 includes a connection 118, such as, for example, a universal serial bus Type C (USB-C) connection and/or the like. The cartridge receptacle 114 portion of the vaporizer body 110 includes one or more openings (air inlets) 116a,b that extend through the outer shell 112 to allow airflow therein, as described in more detail below. The vaporizer body 110 as shown has an elongated, flattened tubular shape that is curvature-continuous, although the vaporizer body 110 is not limited to such a shape. The vaporizer body 110 may take the form of other shapes, such as, for example, a rectangular box, a cylinder, and the like.

The cartridge 150 may fit within the cartridge receptacle 114 by a friction fit, snap fit, and/or other types of secure connection. The cartridge 150 may have a rim, ridge, protrusion, and/or the like for engaging a complimentary portion of the vaporizer body 110. While fitted within the cartridge receptacle 114, the cartridge 150 may be held securely within but still allow for being easily withdrawn to remove the cartridge 150.

Although FIG. 1A-FIG. 1F illustrate a certain configuration of the vaporizer device 100, the vaporizer device 100 may take other configurations as well.

Figure 2:
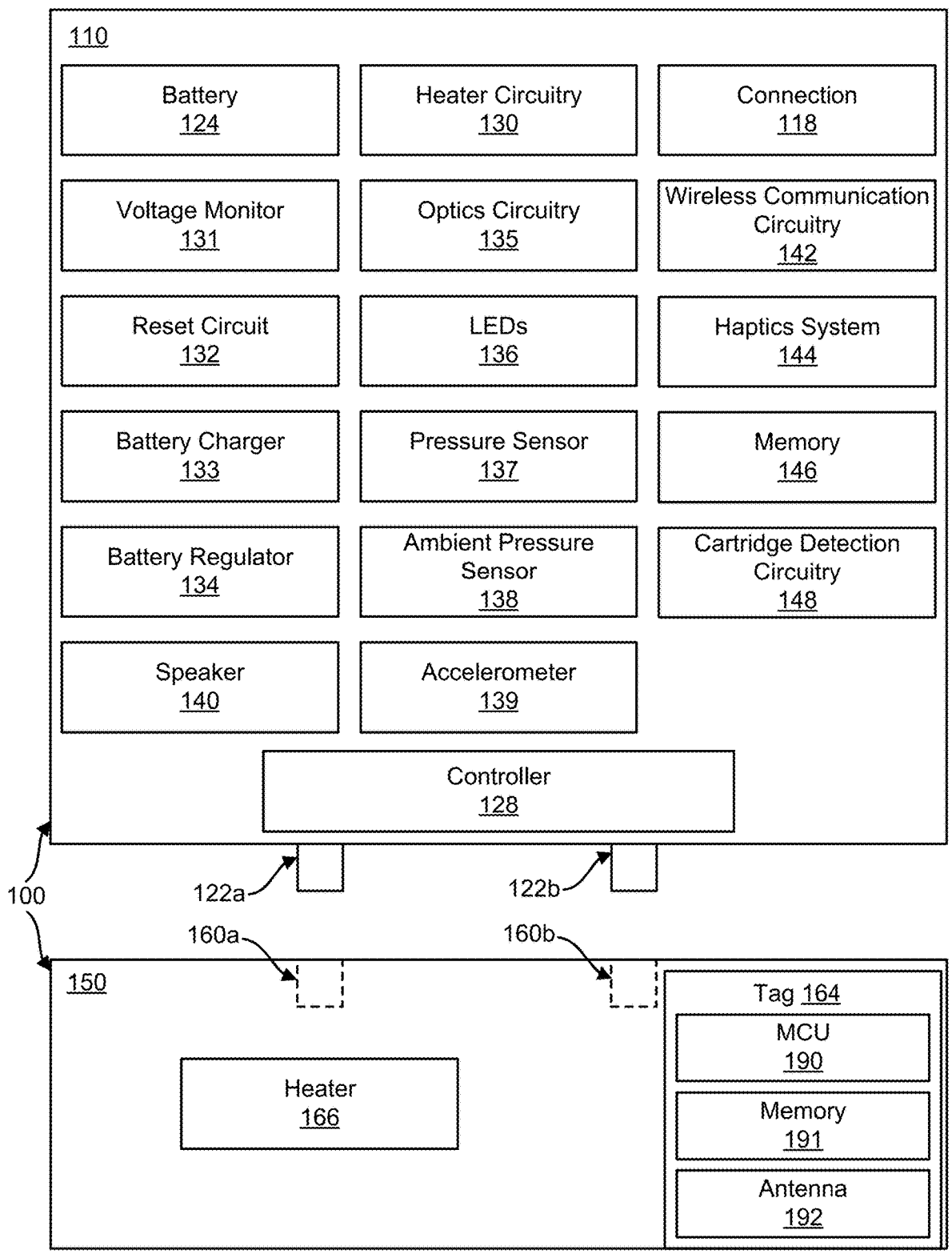
FIG. 2 is a schematic block diagram illustrating features of a vaporizer device having a cartridge and a vaporizer body consistent with implementations of the current subject matter.

FIG. 2 is a schematic block diagram illustrating components of the vaporizer device 100 having the cartridge 150 and the vaporizer body 110 consistent with implementations of the current subject matter. Included in the vaporizer body 110 is a controller 128 that includes at least one processor and/or at least one memory configured to control and manage various operations among the components of the vaporizer device 100 described herein.

Heater control circuitry 130 of the vaporizer body 110 controls a heater 166 of the cartridge 150. The heater 166 may generate heat to provide vaporization of the vaporizable material. For example, the heater 166 may include a heating coil (e.g., a resistive heater) in thermal contact with a wick which absorbs the vaporizable material, as described in further detail below.

A battery 124 is included in the vaporizer body 110, and the controller 128 may control and/or communicate with a voltage monitor 131 which includes circuitry configured to monitor the battery voltage, a reset circuit 132 configured to reset (e.g., shut down the vaporizer device 100 and/or restart the vaporizer device 100 in a certain state), a battery charger 133, and a battery regulator 134 (which may regulate the battery output, regulate charging/discharging of the battery, and provide alerts to indicate when the battery charge is low, etc.).

The power pins 122a,b of the vaporizer body 110 engage the complementary power pin receptacles 160a,b of the cartridge 150 when the cartridge 150 is engaged with the vaporizer body 110. Alternatively, power pins may be part of the cartridge 150 for engaging complementary power pin receptacles of the vaporizer body 110. The engagement allows for the transfer of energy from an internal power source (e.g., the battery 124) to the heater 166 in the cartridge 150. The controller 128 may regulate the power flow (e.g., an amount or current and/or a voltage amount) to control a temperature at which the heater 166 heats the vaporizable material contained in the reservoir 158. According to implementations of the current subject matter, a variety of electrical connectors other than a pogo-pin and complementary pin receptacle configuration may be used to electrically connect the vaporizer body 110 and the cartridge 150, such as for example, a plug and socket connector.

The controller 128 may control and/or communicate with optics circuitry 135 (which controls and/or communicates with one or more displays such as LEDs 136 which may provide user interface output indications), a pressure sensor 137, an ambient pressure sensor 138, an accelerometer 139, and/or a speaker 140 configured to generate sound or other feedback to a user.

The pressure sensor 137 may be configured to sense a user drawing (e.g., inhaling) on the mouthpiece 152 and activate the heater control circuitry 130 of the vaporizer body 110 to accordingly control the heater 166 of the cartridge 150. In this way, the amount of current supplied to the heater 166 may be varied according the user's draw (e.g., additional current may be supplied during a draw, but reduced when there is not a draw taking place). The ambient pressure sensor 138 may be included for atmospheric reference to reduce sensitivity to ambient pressure changes and may be utilized to reduce false positives potentially detected by the pressure sensor 137 when measuring draws from the mouthpiece 152.

The accelerometer 139 (and/or other motion sensors, capacitive sensors, flow sensors, strain gauge(s), or the like) may be used to detect user handling and interaction, for example, to detect movement of the vaporizer body 110 (such as, for example, tapping, rolling, and/or any other deliberate movement associated with the vaporizer body 110).

The vaporizer body 110, as shown in FIG. 2, includes wireless communication circuitry 142 that is connected to and/or controlled by the controller 128. The wireless communication circuitry 142 may include a near-field communication (NFC) antenna that is configured to read from and/or write to the tag 164 of the cartridge 150. Alternatively or additionally, the wireless communication circuitry 142 may be configured to automatically detect the cartridge 150 as it is being inserted into the vaporizer body 110. In some implementations, data exchanges between the vaporizer body 110 and the cartridge 150 take place over NFC. In some implementations, data exchanges between the vaporizer body 110 and the cartridge 150 may take place via a wired connection such as various wired data protocols.

The wireless communication circuitry 142 may include additional components including circuitry for other communication technology modes, such as Bluetooth circuitry, Bluetooth Low Energy circuitry, Wi-Fi circuitry, cellular (e.g., LTE, 4G, and/or 5G) circuitry, and associated circuitry (e.g., control circuitry), for communication with other devices. For example, the vaporizer body 110 may be configured to wirelessly communicate with a remote processor (e.g., a smartphone, a tablet, a computer, wearable electronics, a cloud server, and/or processor based devices) through the wireless communication circuitry 142, and the vaporizer body 110 may through this communication receive information including control information (e.g., for setting temperature, resetting a dose counter, etc.) from and/or transmit output information (e.g., dose information, operational information, error information, temperature setting information, charge/battery information, etc.) to one or more of the remote processors.

The tag 164 may be a type of wireless transceiver and may include a microcontroller unit (MCU) 190, a memory 191, and an antenna 192 (e.g., an NFC antenna) to perform the various functionalities described below with further reference to FIG. 3. The tag 164 may be, for example, a 1 Kbit or a 2 Kbit NFC tag that is of type ISO/IEC 15693. NFC tags with other specifications may also be used. The tag 164 may be implemented as active NFC, enabling reading and/or writing information via NFC with other NFC compatible devices including a remote processor, another vaporizer device, and/or wireless communication circuitry 142. Alternatively, the tag 164 may be implemented using passive NFC technology, in which case other NFC compatible devices (e.g., a remote processor, another vaporizer device, and/or wireless communication circuitry 142) may only be able to read information from the tag 164.

The vaporizer body 110 may include a haptics system 144, such as an actuator, a linear resonant actuator (LRA), an eccentric rotating mass (ERM) motor, or the like that provide haptic feedback such as a vibration as a "find my device" feature or as a control or other type of user feedback signal. For example, using an app running on a user device (such as, for example, a user device 305 shown in FIG. 3), a user may indicate that he/she cannot locate his/her vaporizer device 100. Through communication via the wireless communication circuitry 142, the controller 128 sends a signal to the haptics system 144, instructing the haptics system 144 to provide haptic feedback (e.g., a vibration). The controller 128 may additionally or alternatively provide a signal to the speaker 140 to emit a sound or series of sounds. The haptics system 144 and/or speaker 140 may also provide control and usage feedback to the user of the vaporizer device 100; for example, providing haptic and/or audio feedback when a particular amount of a vaporizable material has been used or when a period of time since last use has elapsed. Alternatively or additionally, haptic and/or audio feedback may be provided as a user cycles through various settings of the vaporizer device 100. Alternatively or additionally, the haptics system 144 and/or speaker 140 may signal when a certain amount of battery power is left (e.g., a low battery warning and recharge needed warning) and/or when a certain amount of vaporizable material remains (e.g., a low vaporizable material warning and/or time to replace the cartridge 150). Alternatively or additionally, the haptics system 144 and/or speaker 140 may also provide usage feedback and/or control of the configuration of the vaporizer device 100 (e.g., allowing the change of a configuration, such as target heating rate, heating rate, etc.).

The vaporizer body 110 may include circuitry for sensing/detecting when a cartridge 150 is connected and/or removed from the vaporizer body 110. For example, cartridge-detection circuitry 148 may determine when the cartridge 150 is connected to the vaporizer body 110 based on an electrical state of the power pins 122a,b within the cartridge receptacle 114. For example, when the cartridge 150 is present, there may be a certain voltage, current, and/or resistance associated with the power pins 122a,b, when compared to when the cartridge 150 is not present. Alternatively or additionally, the tag 164 may also be used to detect when the cartridge 150 is connected to the vaporizer body 110.

The vaporizer body 110 also includes the connection (e.g., USB-C connection, micro-USB connection, and/or other types of connectors) 118 for coupling the vaporizer body 110 to a charger to enable charging the internal battery 124. Alternatively or additionally, electrical inductive charging (also referred to as wireless charging) may be used, in which case the vaporizer body 110 would include inductive charging circuitry to enable charging. The connection 118 at FIG. 2 may also be used for a data connection between a computing device and the controller 128, which may facilitate development activities such as, for example, programming and debugging, for example.

The vaporizer body 110 may also include a memory 146 that is part of the controller 128 or is in communication with the controller 128. The memory 146 may include volatile and/or non-volatile memory or provide data storage. In some implementations, the memory 146 may include 8 Mbit of flash memory, although the memory is not limited to this and other types of memory may be implemented as well.

In operation, after the vaporizer device 100 is charged, a user may activate the vaporizer device 100 by drawing (e.g., inhaling) through the mouthpiece. The vaporizer device 100 may detect a draw (e.g., using a pressure sensor, flow sensors, and/or the like, including a sensor configured to detect a change in temperature or power applied to a heater element) and may increase the power to a predetermined temperature preset. The power may be regulated by the controller by detecting the change in resistance of the heating coil and using the temperature coefficient of resistivity to determine the temperature.

In accordance with some implementations of the current subject matter, the vaporizer device 100 may be controlled so that the temperature used to vaporize the vaporizable material is maintained within a preset range. In general, the controller may control the temperature of the resistive heater (e.g., resistive coil, etc.) based on a change in resistance due to temperature (e.g., temperature coefficient of resistance (TCR)). For example, a heater may be any appropriate resistive heater, such as, for example, a resistive coil. The heater is typically coupled to the heater controller via two or more connectors (electrically conductive wires or lines) so that the heater controller applies power (e.g., from the power source) to the heater. The heater controller may include regulatory control logic to regulate the temperature of the heater by adjusting the applied power. The heater controller may include a dedicated or general-purpose processor, circuitry, or the like and is generally connected to the power source and may receive input from the power source to regulate the applied power to the heater.

Figure 3:
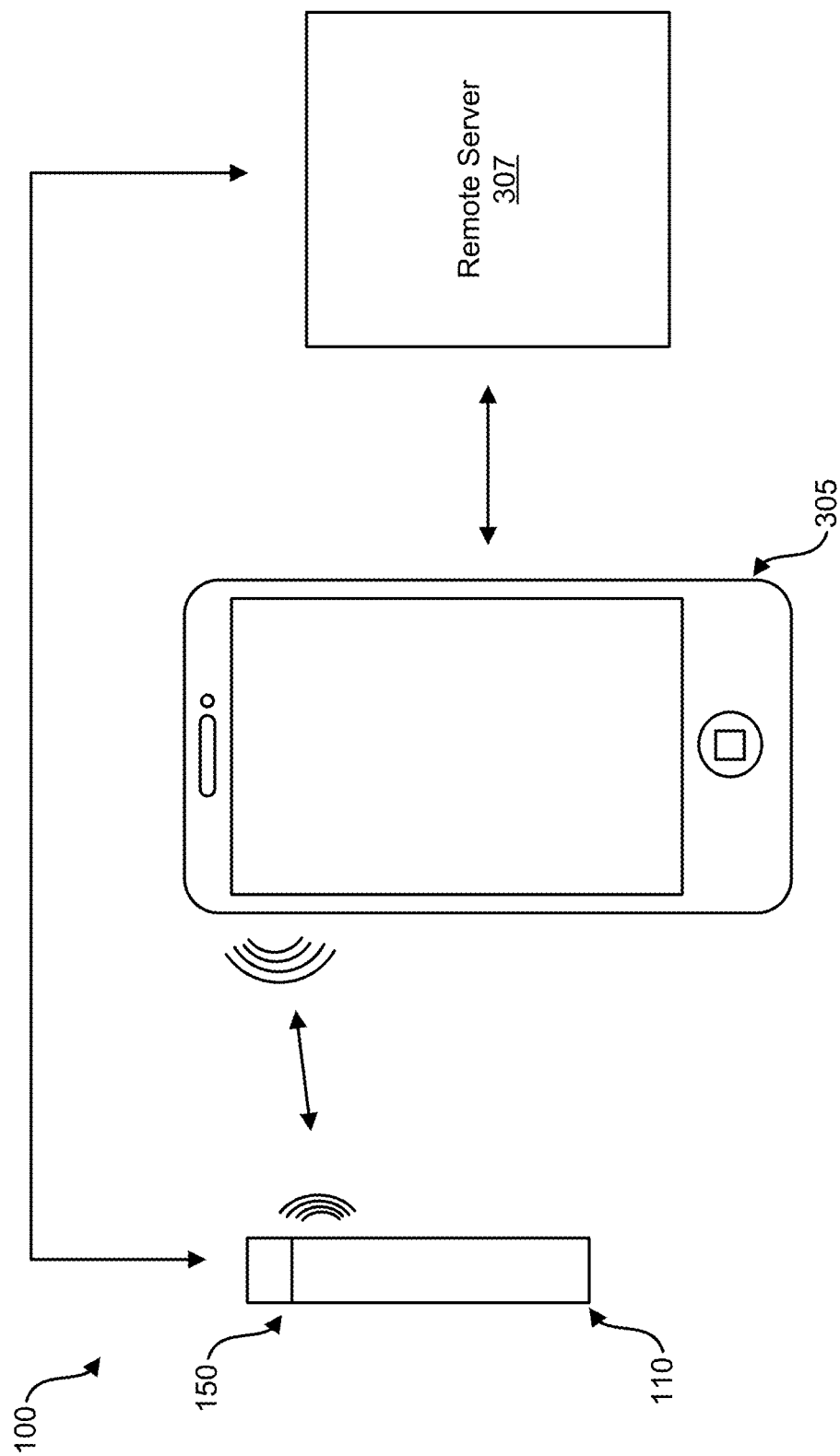
FIG. 3 illustrates communication between a vaporizer device, a user device, and a server consistent with implementations of the current subject matter.

FIG. 3 illustrates communication between the vaporizer device 100 (including the vaporizer body 110 and the cartridge 150), the user device 305 (e.g., a smartphone, tablet, laptop, desktop computer, a workstation, and/or the like), and a remote server 307 (e.g., a server coupled to a network, a cloud server coupled to the Internet, and/or the like) consistent with implementations of the current subject matter. The user device 305 wirelessly communicates with the vaporizer device 100. A remote server 307 may communicate directly with the vaporizer device 100 or through the user device 305. The vaporizer body 110 may communicate with the user device 305 and/or the remote server 307 through the wireless communication circuitry 142. In some implementations, the cartridge 150 may establish through the tag 164 communication with the vaporizer body 110, the user device 305, and/or the remote server 307. While the user device 305 in FIG. 3 is depicted as a type of handheld mobile device, the user device 305 consistent with implementations of the current subject matter is not so limited and may be, as indicated, various other types of user computing devices.

An application software ("app") running on at least one of the remote processors (the user device 305 and/or the remote server 307) may be configured to control operational aspects of the vaporizer device 100 and receive information relating to operation of the vaporizer device 100. For example, the app may provide a user with capabilities to input or set desired properties or effects, such as, for example, a particular temperature or desired dose, which is then communicated to the controller 128 of the vaporizer body 110 through the wireless communication circuitry 142. The app may also provide a user with functionality to select one or more sets of suggested properties or effects that may be based on the particular type of vaporizable material in the cartridge 150. For example, the app may allow adjusting heating based on the type of vaporizable material, the user's (of the vaporizer device 100) preferences or desired experience, and/or the like. The app may be a mobile app and/or a browser-based or web app. For example, the functionality of the app may be accessible through one or more web browsers running on one or more types of user computing devices.

Data read from the tag 164 from the wireless communication circuitry 142 of the vaporizer body 110 may be transferred to one or more of the remote processors (e.g., the user device 305 and/or the remote server 307) to which it is connected, which allows for the app running on the one or more processors to access and utilize the read data for a variety of purposes. For example, the read data relating to the cartridge 150 may be used for providing recommended temperatures, dose control, usage tracking, and/or assembly information.

The cartridge 150 may also communicate directly, through the tag 164, with other devices. This enables data relating to the cartridge 150 to be written to/read from the tag 164, without interfacing with the vaporizer body 110. The tag 164 thus allows for identifying information (e.g., pod ID, batch ID, etc.) related to the cartridge 150 to be associated with the cartridge 150 by one or more remote processors. For example, when the cartridge 150 is filled with a certain type of vaporizable material, this information may be transmitted to the tag 164 by filling equipment. Then, the vaporizer body 110 is able to obtain this information from the tag 164 (e.g., via the wireless communication circuitry 142 at the vaporizer body 110) to identify the vaporizable material currently being used and accordingly adjust the controller 128 based on, for example, user-defined criteria or pre-set parameters associated with the particular type of vaporizable material (set by a manufacturer or as determined based upon user experiences/feedback aggregated from other users). For example, a user may establish (via the app) a set of criteria relating to desired effects for or usage of one or more types of vaporizable materials. When a certain vaporizable material is identified, based on communication via the tag 164, the controller 128 may accordingly adopt the established set of criteria, which may include, for example, temperature and dose, for that particular vaporizable material.

As described above, the vaporizer device 100 and/or the user device 305 that is part of a vaporizer system as defined above may include a user interface (e.g., including an app or application software) that may be executed on the user device 305 in communication, which may be configured to determine, display, enforce, and/or meter dosing.

The vaporizer device 100 consistent with implementations of the current subject matter may be configured to facilitate social interaction through the vaporizer device 100. For example, the vaporizer device 100 may be configured to share usage information with others, such as third parties including health care providers, etc., for better prescription and administration of medical treatment. The vaporizer device 100 may also be configured to communicate with non-medical third parties (e.g., friends, colleagues, etc.), and with unknown third parties (making some or all information publically available). In some implementations, the vaporizer device 100 described herein, either by itself or in communication with one or more communications devices that are part of a system, may identify and provide information about the operation, status, or user input from the vaporizer device 100 to a public or private network.

Software, firmware, or hardware that is separate or separable from the vaporizer device and that wirelessly communicates with the vaporizer device 100 may be provided as described with respect to FIG. 3. For example, applications ("apps") may be executed on a processor of a desktop device or station and/or a portable and/or wearable device, including smartphones, smartwatches, and the like, which may be referred to as a personal digital device, a user device, or optionally just a device (e.g., user device 305 in FIG. 3) that is part of a connected system. The user device 305 may provide an interface for the user to engage and interact with functions related to the vaporizer device 100, including communication of data to and from the vaporizer device 100 to the user device 305 and/or additional third party processor (e.g., servers such as the remote server 307 in FIG. 3). For example, a user may control some aspects of the vaporizer device 100 (temperature, session size, etc.) and/or data transmission and data receiving to and from the vaporizer device 100, optionally over a wireless communication channel between first communication hardware of the user device 305 and second communication hardware of the vaporizer device 100. Data may be communicated in response to one or more actions of the user (e.g., including interactions with a user interface displayed on the user device 305), and/or as a background operation such that the user does not have to initiate or authorize the data communication process.

User interfaces may be deployed on the user device 305 and may aid the user in operating the vaporizer device 100. For example, the user interface operating on the user device 305 may include icons and text elements that may inform the user of various ways that settings may be adjusted or configured by the user. In this manner (or in others consistent with the current subject matter) information about the vaporizer device 100 may be presented using a user interface displayed by the user device 305. Icons and/or text elements may be provided to allow the user to see information regarding one or more statuses of the vaporizer device 100, such as battery information (charge remaining, draws remaining, time to charge, charging, etc.), cartridge status (e.g., type of cartridge and vaporizable material, fill status of cartridge, etc.), and other device statuses or information. Icons and/or text elements may be provided to allow the user to update internal software (a.k.a., firmware) in the vaporizer device 100. Icons and text elements may be provided to allow the user to set security and/or authorization features of the vaporizer device 100, such as setting a PIN code to activate the vaporizer device 100 or the use of personal biometric information as a way of authentication. Icons and text elements may be provided to allow the user to configure foreground data sharing and related settings.

The vaporizer device 100 may perform onboard data gathering, data analysis, and/or data transmission methods. As mentioned, the vaporizer device 100 having wired or wireless communication capability may interface with digital consumer technology products such as smart phones, tablet computers, laptop/netbook/desktop computers, wearable wireless technologies such as "smart watches," and other wearable technology such as Google "Glass," or similar through the use of programming, software, firmware, GUI, wireless communication, wired communication, and/or software commonly referred to as application(s) or "apps." A wired communication connection may be used to interface the vaporizer device 100 to digital consumer technology products for the purpose of the transmission and exchange of data to/from the vaporizer device from/to the digital consumer technology products (and thereby also interfacing with apps running on the digital consumer technology products). A wireless communication connection may be used to interface the vaporizer device 100 to digital consumer technology products for the transmission and exchange of data to/from the vaporizer device 100 from/to the digital wireless interface. The vaporizer device may use a wireless interface that includes one or more of an infrared (IR) transmitter, a Bluetooth interface, an 802.11 specified interface, and/or communications with a cellular telephone network in order to communicate with consumer technology.

Consistent with implementations of the current subject matter, the vaporizable material used with the vaporizer device may be provided within the cartridge. The vaporizer device may be a cartridge-using vaporizer device or a multi-use vaporizer device capable of use with or without a cartridge. For example, a multi-use vaporizer device may include a heating chamber (e.g., an oven) configured to receive the vaporizable material directly in the heating chamber and also configured to receive the cartridge having a reservoir or the like for holding the vaporizable material. In various implementations, the vaporizer device may be configured for use with liquid vaporizable material (e.g., a carrier solution in which an active and/or inactive ingredient(s) are suspended or held in solution or a liquid form of the vaporizable material itself) or solid vaporizable material. Solid vaporizable material may include a plant material that emits some part of the plant material as the vaporizable material (e.g., such that some part of the plant material remains as waste after the vaporizable material is emitted for inhalation by a user) or optionally may be a solid form of the vaporizable material itself such that all of the solid material may eventually be vaporized for inhalation. Liquid vaporizable material may likewise be capable of being completely vaporized or may include some part of the liquid material that remains after all of the material suitable for inhalation has been consumed.

Aspects of the current subject matter relating to temperature adjustment of a vaporizer device are not limited to use with the particular and/or exact configurations and/or components of the vaporizer device 100, the vaporizer body 110, and the cartridge 150 described with reference to FIG. 1A-FIG. 3. Rather, the foregoing descriptions are provided as examples in which the described aspects may be utilized. Variations of the example vaporizer devices described herein may be used with aspects of the current subject matter directed to temperature adjustment. For example, in one implementation, a single-use integrated vaporizer device may employ the aspects of temperature adjustment consistent with implementations of the current subject matter. Aspects of the current subject matter may be employed with various other vaporizer devices, vaporizer bodies, and cartridges and/or with various modifications of the vaporizer device 100, the vaporizer body 110, and the cartridge 150 described herein. For example, consistent with implementations of the current subject matter, various sensors and circuitry may not be required for the operations provided herein. For example, the ambient pressure sensor 138 and the accelerometer 139 may not be required in some implementations. Various other combinations of configurations and/or components of the vaporizer device 100, the vaporizer body 110, and the cartridge 150 may be employed consistent with implementations of the current subject matter.

Additionally, while some implementations of the current subject matter may be described with respect to cannabis and cannabinoid-based vaporizable materials, for example cannabis oils, the disclosure is not limited to cannabis and cannabinoid-based vaporizable materials and may be applicable to other types of materials.

Turning to temperature adjustment of the vaporizer device 100, consistent with implementations of the current subject matter, user controlled actions with respect to removing the cartridge 150 from and inserting the cartridge 150 into the cartridge receptacle 114 provide for adjusting the temperature of the vaporizer device 100. The temperature refers to a setpoint temperature of operation of the vaporizer device 100 (e.g., the temperature at which the heater 166 operates to vaporize the vaporizable material contained in the cartridge 150).

The temperature adjustment aspects of the current subject matter provide a user with a controlled, intuitive, and simple method to adjust the setpoint temperature of the vaporizer device 100. Moreover, the temperature adjustment aspects provide for quickly incrementing through a sequence of setpoint temperatures, allowing the user to select the desired setpoint temperature for use with the vaporizer device 100. According to aspects of the current subject matter, insertion and removal of the cartridge 150 into and from the cartridge receptacle 114 of the vaporizer body 110 causes the setpoint temperature to cycle through the sequence of setpoint temperatures, as described further herein. The temperature adjustment aspects of the current subject matter do not require use of the app on the user device 305 or a web-based application, nor do they require an accelerometer, such as the accelerometer 139 shown in FIG. 2.

According to aspects of the current subject matter, the temperature adjustment features may be automatically initiated upon the insert and remove steps described herein. In some implementations, the temperature adjustment features may be turned on and off through, for example, a predefined action with respect to the cartridge 150 and/or the vaporizer body 110 and/or an app running on the user device 305 connected to the vaporizer device 100.

According to aspects of the current subject matter, a preset setpoint temperature may be used as a starting point for the temperature adjustment of the vaporizer device 100. For example, the preset setpoint temperature may be the first or initial setpoint temperature for the vaporizer device 100 when the cartridge 150 is initially (e.g., after a period of time during which the vaporizer device 100 has not been used) inserted into the vaporizer body 110. The preset setpoint temperature may be user, device, or cartridge defined and/or may be based on various factors such as for example user preferences, crowdsourced information, type of vaporizable material, and/or the like. The preset setpoint temperature may be a default setting (e.g., a default provided by the vaporizer device 100, a default corresponding to the vaporizable material (e.g., a strain of cannabinoids), or a default corresponding to the cartridge 150). The preset setpoint temperature may carry over from a previous use of the vaporizer device 100 and/or the cartridge 150. The preset setpoint temperature may be defined and/or updated by the user using the app running on the user device 305 or using a web-based application on a mobile device or a desktop device. The preset setpoint temperature may be the first temperature in a sequence of setpoint temperatures, as further described herein.

As one example, the preset setpoint temperature may be the most recent setpoint temperature used with the cartridge 150 and/or the vaporizer body 110. For example, the most recent setpoint temperature may be stored in the memory 146 of the vaporizer body 110 and associated with the cartridge 150 based on an identifier of the cartridge 150 that is read by the controller 128 from the tag 164 of the cartridge 150. When the controller 128, through the wireless communication circuitry 142, recognizes the cartridge 150, the controller 128 may access from the memory 146 the most recent setpoint temperature and use this as the preset setpoint temperature. Alternatively, the controller 128 may read the most recent setpoint temperature from the tag 164 of the cartridge 150.

As an additional and/or alternative example, the preset setpoint temperature may be associated with the cartridge 150 based on various factors, such as the type of vaporizable material (e.g., a manufacturer defines the preset setpoint temperature for the cartridge 150). The preset setpoint temperature may be stored on the tag 164 of the cartridge 150 and read by the controller 128.

According to aspects of the current subject matter, user controlled actions of the cartridge 150 inserted into and removed from the vaporizer body 110 establish the setpoint temperature of the vaporizer device 100. In particular, when the cartridge 150 is inserted into the vaporizer body 110, the cartridge 150 is detected by, for example, the cartridge detection circuitry 148 or by other detection means. Upon detection of the cartridge 150, the vaporizer body 110 may determine or identify the preset setpoint temperature as described above. For example, the controller 128 of the vaporizer body 110 may use a default preset setpoint temperature, the preset setpoint temperature associated with the cartridge 150 and/or the vaporizer body 110, the most recent setpoint temperature used with the cartridge 150 and/or the vaporizer body 110, and/or a user defined preset setpoint temperature (e.g., as defined through use of the app or web-based application). In some implementations of the current subject matter, one or more of the preset setpoint temperature options may take priority over the others. For example, the default preset setpoint temperature may have a low priority such that the preset setpoint temperature associated with the cartridge 150 takes precedence in setting the preset setpoint temperature. The user defined preset setpoint temperature may override the other preset setpoint temperature options. The priority may be predefined, user-defined, and/or user-adjustable. For example, the user may define and/or adjust the priority using the app and/or the web-based application.

Once the preset setpoint temperature is determined, with the cartridge 150 in the vaporizer body 110, the user may begin puffing on the mouthpiece of the cartridge 150, which may serve to activate the heater 166 to reach the preset setpoint temperature for vaporization.

Consistent with implementations of the current subject matter, after the cartridge 150 is inserted into the vaporizer body 110 and prior to the user using the vaporizer device 100 for consumption of vapor, the user may remove the cartridge 150 from the vaporizer body 110. The removal of the cartridge 150 may be detected by the cartridge detection circuitry 148 or other detection means. The removal of the cartridge 150, consistent with implementations of the current subject matter, may initiate a timeout period during which inserting the cartridge 150 back into the vaporizer body 110 results in the preset setpoint temperature incrementing to a next setpoint temperature in a sequence or series of setpoint temperatures. The sequence of setpoint temperatures may include a plurality of temperatures in a defined order. Consistent with implementations of the current subject matter, the sequence of setpoint temperatures may be established such that cartridge removal and insertion causes the setpoint temperature to increment through the sequence of setpoint temperatures, based on the timeout period, with each remove and insert operation.

For example, a plurality of setpoint temperatures may be established for the vaporizer device 100. The initial insertion of the cartridge 150 into the vaporizer body 110 results in the preset setpoint temperature being identified. Removal of the cartridge 150 followed by reinsertion of the cartridge 150 during the timeout period results in the preset setpoint temperature incrementing to the next setpoint temperature. Continuing this process, a subsequent removal and reinsertion of the cartridge 150 during a new timeout period results in the setpoint temperature incrementing to the next setpoint temperature. This process may continue indefinitely with the setpoint temperature incrementing to the next setpoint temperature in the sequence of setpoint temperatures. The sequence of setpoint temperatures may be such that when the highest setpoint temperature is reached, the next setpoint temperature in the sequence of setpoint temperatures is the lowest setpoint temperature. For example, the sequence of setpoint temperatures may be 270° C., 320° C., 370° C., and 420° C. If the preset setpoint temperature for the cartridge 150 and/or the vaporizer body 110 is 320° C., the setpoint temperature may increment (with the cartridge removal and insertion process consistent with implementations of the current subject matter) to 370° C., followed by 420° C., followed by 270° C., followed by 320° C., and so on until the user leaves the cartridge 150 in the vaporizer body 110 or until the user does not reinsert the cartridge 150 during the timeout period.

The sequence of setpoint temperatures including 270° C., 320° C., 370° C., and 420° C. is just one example, and implementations of the current subject matter are not limited to this particular sequence. The sequence may be based on the user, the cartridge 150, the vaporizer body 110, and the sequence may be predefined, user-defined, and/or user-adjustable. Additionally, the sequence is not limited to four values, and fewer or additional values may be included in the sequence of setpoint temperatures. The values in the sequence of setpoint temperatures need not be equally spaced apart. For example, an example sequence of setpoint temperatures may be 250° C., 320° C., 370° C., and 430° C. The values in the sequence of setpoint temperatures need not increase in numerical order but can be in any desired order. For example, a user may have a number of preferred setpoint temperatures, and may create (e.g., though use of the app running on the user device 305) the sequence of setpoint temperatures based on the preferred setpoint temperatures. Moreover, the values may be represented in degrees Fahrenheit, where one example sequence of setpoint temperatures includes 520° F., 610° F., 700° F., and 790° F.

With respect to the timeout period, the timeout period may be, consistent with implementations of the current subject matter, reset each time the cartridge 150 is removed from the vaporizer body 110. The timeout period may be predefined, user-defined, and/or user-adjustable. In some implementations, the timeout period is one second. In other implementations, the timeout period may be about 0.5 seconds, about 0.6 seconds, about 0.7 seconds, about 0.8 seconds, about 0.9 seconds, about 1.1 seconds, about 1.2 seconds, about 1.3 seconds, about 1.4 seconds, or about 1.5 seconds; though the timeout period is not limited to any particular value, and any value can be used with implementations of the current subject matter.

Consistent with implementations of the current subject matter, after the timeout period has elapsed (e.g., the user leaves the cartridge 150 in the vaporizer body 110), the selected setpoint temperature is the temperature to which the heater 166 heats to produce vapor for consumption by the user. Consistent with implementations of the current subject matter, if the user does not reinsert the cartridge 150 during the timeout period, and then later inserts the cartridge 150 into the vaporizer body 110, the preset setpoint temperature is identified and used for the start of the sequence of setpoint temperatures.

In some instances, the preset setpoint temperature may not coincide or match with one of the setpoint temperatures in the sequence of setpoint temperatures. For example, a preset setpoint temperature may be associated with the cartridge 150 (referred to herein as a cartridge-associated setpoint temperature) and/or defined by the user using the app or a web-based application (referred to herein as a user-defined setpoint temperature). The cartridge-associated setpoint temperature and/or the user-defined setpoint temperature may be a value other than one of the setpoint temperatures in the sequence. According to implementations of the current subject matter, the sequence of setpoint temperatures may be expanded to include the cartridge-associated setpoint temperature and/or the user-defined setpoint temperature.

For example, as previously described, the cartridge 150 may have associated with it, based on various factors such as the type of vaporizable material, a preset setpoint temperature. The preset setpoint temperature may be written to and stored on the tag 164 of the cartridge 150 and accessible to the controller 128 via the wireless communication circuitry 142. In other instances, the user may set a desired preset setpoint temperature using, for example, the app running on the user device 305 or a web-based application. In either instance, it may be desirable and/or beneficial to the user to have the option of selecting the cartridge-associated setpoint temperature and/or the user-defined setpoint temperature. Thus, consistent with implementations of the current subject matter, the cartridge-associated setpoint temperature and/or the user-defined setpoint temperature may form part of the sequence of setpoint temperatures.

For example, in an implementation, the cartridge-associated setpoint temperature and/or the user-defined setpoint temperature may be set as the last temperature in the sequence (when viewing the sequence as low to high temperatures). As an example, the cartridge-associated setpoint temperature may be 320° C. Continuing the example in which the sequence is 270° C., 320° C., 370° C., and 420° C., the sequence with the cartridge-associated setpoint temperature is then 270° C., 320° C., 370° C., 420° C., 320° C. (e.g., the cartridge-associated setpoint temperature at the end position in the sequence), repeat. In an implementation, the cartridge-associated setpoint temperature and/or the user-defined setpoint temperature may be positioned in the sequence based on its value. Using the same example as above, the sequence would then be 270° C., 320° C., 320° C. (e.g., the cartridge-associated setpoint temperature), 370° C., and 420° C., repeat. In another implementation, the cartridge-associated setpoint temperature and/or the user-defined setpoint temperature may be set as the first temperature in the sequence. For example, if the cartridge-associated setpoint temperature is set to 320° C., the sequence would be 320° C. (e.g., the cartridge-associated setpoint temperature), 270° C., 320° C., 370° C., 420° C., repeat.

The cartridge-associated setpoint temperature and/or the user-defined setpoint temperature may be any unique value and may be a value different than the values of the setpoint temperatures in the sequence of setpoint temperatures. For example, the cartridge-associated setpoint temperature may be 300° C. If the cartridge-associated setpoint temperature is placed at the end of the sequence, then the example sequence (continuing the example above) is 270° C., 320° C., 370° C., 420° C., 300° C. (e.g., the cartridge-associated setpoint temperature at the end position in the sequence), repeat. If the cartridge-associated setpoint temperature is placed in the sequence based on its value, then the example sequence (continuing the example above) is 270° C., 300° C. (e.g., the cartridge-associated setpoint temperature), 320° C., 370° C., and 420° C., repeat. If the cartridge-associated setpoint temperature is placed at the beginning of the sequence, then the example sequence (continuing the example above) is 300° C. (e.g., the cartridge-associated setpoint temperature), 270° C., 320° C., 370° C., 420° C., repeat.

In some implementations, both the cartridge-associated setpoint temperature and the user-defined setpoint temperature may be incorporated in the sequence of setpoint temperatures. For example, a cartridge-associated setpoint temperature may be defined for the cartridge 150, and the user may additionally set a user-defined setpoint temperature. The cartridge-associated setpoint temperature and the user-defined setpoint temperature may be the same as one another or different from one another. One or both of the cartridge-associated setpoint temperature and the user-defined setpoint temperature may equal one of the setpoint temperatures in the sequence of setpoint temperatures. Consistent with implementations of the current subject matter, the cartridge-associated setpoint temperature and the user-defined setpoint temperature may be incorporated in the sequence of setpoint temperatures based on their values, or may be incorporated in the sequence of setpoint temperatures in defined positions (e.g., as the first two, as the last two, or at any position that is predefined or set by the user or that is a default setting). In some implementations, if the cartridge-associated setpoint temperature and the user-defined setpoint temperature are the same value, that value may be incorporated once in the sequence of setpoint temperatures or twice in the sequence of setpoint temperatures.

In yet another implementation, the user-defined setpoint temperature may be positioned at the beginning of the sequence and the cartridge-associated setpoint temperature may be positioned at the end of the sequence. For example, the sequence may be the user-defined setpoint temperature, 270° C., 320° C., 370° C., 420° C., and the cartridge-associated setpoint temperature. In some implementations, the cartridge-associated setpoint temperature may be positioned at the beginning of the sequence and the user-defined setpoint temperature may be positioned at the end of the sequence.

In accordance with implementations of the current subject matter, if the user-defined setpoint temperature is not selected by the user during the first cycle through the sequence of setpoint temperatures, the user-defined setpoint temperature may be removed from the sequence when the user cycles through the sequence again. For example, in this instance, the sequence may be the user-defined setpoint temperature, 270° C., 320° C., 370° C., 420° C., the cartridge-associated setpoint temperature, 270° C., 320° C., 370° C., 420° C., the cartridge-associated setpoint temperature, repeat. In some implementations, if the cartridge-associated setpoint temperature is not selected by the user, the cartridge-associated setpoint temperature may be removed from the sequence when the user cycles through the sequence again.

Consistent with implementations of the current subject matter, aspects of the user-defined setpoint temperature and the cartridge-associated setpoint temperature and the incorporation of both into the sequence of setpoint temperatures may be based on default settings and/or may be user-defined and/or user-adjustable. For example, the value of the user-defined setpoint temperature, the position of the user-defined setpoint temperature and/or the cartridge-associated setpoint temperature in the sequence, and/or the removal or inclusion of the user-defined setpoint temperature and/or the cartridge-associated setpoint temperature in the sequence after the first cycle through the sequence, may be defined by default settings and/or may be user-defined and/or user-adjustable.

In addition to setting the setpoint temperature of the vaporizer device 100, consistent with implementations of the current subject matter, a visual indication of the temperature adjustment and the setpoint temperature is provided by the LEDs 136 of the vaporizer body 110. For example, upon detection of the cartridge 150 in the vaporizer body 110 and determination of the setpoint temperature (e.g., the preset setpoint temperature or the setpoint temperature in the sequence of setpoint temperatures established by the remove and insert process), an indication of the setpoint temperature may be provided by the LEDs 136. Removal of the cartridge 150 may result in an indication of the removal of the cartridge 150 being portrayed by the LEDs 136. According to some implementations, a length of time of the indication of the removal of the cartridge 150 may be equal to the timeout period. This may allow, for example, the user to visually see if there is time remaining in the timeout period.

Moreover, incrementing through the sequence of setpoint temperatures may also be portrayed by the LEDs 136. For example, illumination and/or fading of the LEDs 136 in various combinations may signify the setpoint temperature, removal of the cartridge 150, insertion of the cartridge 150, the cartridge-associated setpoint temperature, the user-defined setpoint temperature, and/or incrementing through the sequence of the setpoint temperatures. FIG. 5A-FIG. 5F, described below, provide example representations of the temperature adjustment features being portrayed by the LEDs 136 consistent with implementations of the current subject matter.

With reference to FIG. 4, a process flow chart 400 is provided to illustrate features of temperature adjustment consistent with some implementations of the current subject matter.

At 405, the cartridge 150 is detected as being contained or present in the vaporizer body 110. For example, the cartridge detection circuitry 148 may detect that the cartridge 150 is inserted into the cartridge receptacle 114 due to a connection made between the power pins 122*a,b* and the power pin receptacles 160*a,b*.

At 410, the setpoint temperature (e.g., the preset setpoint temperature) is determined. For example, the setpoint temperature may be the default setpoint temperature, the cartridge-associated setpoint temperature (if applicable), the user-defined setpoint temperature, the setpoint temperature carried over from the previous use of the vaporizer device 100 and/or the cartridge 150, or the first setpoint temperature in a sequence of setpoint temperatures.

At 415, the setpoint temperature may be indicated on the vaporizer device 100. For example, the detection of the cartridge 150 and the determination or identification of the setpoint temperature may be portrayed by the LEDs 136 with a predefined illumination, which may include illumination and/or fading of the LEDs 136. For example, a display of the vaporizer body 110 may include the LEDs 136, and a predefined pattern of illumination of the LEDs 136 may correspond to the setpoint temperature. Each setpoint temperature may have a corresponding predefined pattern of illumination of the LEDs 136 such that a particular pattern indicates one setpoint temperature while another pattern is indicative of another setpoint temperature. Moreover, the predefined pattern of illumination may indicate a position within the sequence of setpoint temperatures. For example, a first setpoint temperature may be represented by one flash of the LEDs 136 or a lighter-colored illumination.

Additionally, the detection of the cartridge 150 may be represented by the LEDs 136 with a predefined cartridge detection illumination, which may include illumination and/or fading of the LEDs 136. Consistent with implementations of the current subject matter, the predefined cartridge detection illumination may occur upon cartridge detection (e.g., after the timeout period has elapsed or during the timeout period), signifying a new start or resumption of the temperature adjustment features according to aspects of the current subject matter. The predefined cartridge detection illumination may occur for a given length of time (referred to herein as a cartridge detection period) that may be equal to the timeout period or may be shorter or longer than the timeout period. The cartridge detection period may be predefined and/or user adjustable. In some implementations, the cartridge detection period is one second. In other implementations, the cartridge detection period may be about 0.5 seconds, about 0.6 seconds, about 0.7 seconds, about 0.8 seconds, about 0.9 seconds, about 1.1 seconds, about 1.2 seconds, about 1.3 seconds, about 1.4 seconds, or about 1.5 seconds; though the cartridge detection period is not limited to any particular value, and any value can be used with implementations of the current subject matter.

Moreover, a haptic feedback may also be provided to indicate insertion of the cartridge 150, identification of the setpoint temperature, and/or removal of the cartridge 150. The haptic feedback may be a pulse or vibration provided by the haptics system 144. According to aspects of the current subject matter, each setpoint temperature may have a corresponding predefined haptic feedback to indicate to the user the respective setpoint temperature. The predefined haptic feedback may also indicate a position within the sequence of setpoint temperatures. For example, a single pulse may be representative of a first setpoint temperature within the sequence of setpoint temperatures. A predefined haptic feedback may also be provided for cartridge detection after the timeout period has elapsed, thus signifying through the haptic feedback a new start of the temperature adjustment features. A predefined haptic feedback may also be provided for cartridge removal. The duration of the haptic feedback may directly correspond to and/or equal a length of time of the corresponding illumination of the LEDs 136. For example, removal of the cartridge 150 may be represented by haptic feedback that is equal in duration to the timeout period. Detection of the cartridge 150 may be represented by haptic feedback that is equal in duration to the cartridge detection period. The haptic feedback that represents the setpoint temperatures may correspond in duration to the length in time in which the LEDs 136 are illuminated for the particular setpoint temperature. In some implementations, duration of the haptic feedback is not related to the action (e.g., cartridge detection, cartridge removal, determination of setpoint temperature) but may instead be a single pulse or other defined haptic pattern.

As previously noted, the temperature adjustment aspects of the current subject matter do not require use of the app on the user device 305. However, if the user device 305 is connected to the vaporizer device 100 and the app is running, an indication of the temperature adjustment process may be provided on an interface of the user device 305. For example, at 420, an indication of the setpoint temperature may be provided on the user device 305.

At 425, removal of the cartridge 150 from the vaporizer body 110 is detected. For example, the cartridge detection circuitry 148 may detect a disconnection or loss of connection between the power pins 122*a,b* and the power pin receptacles 160*a,b*.

At 430, the removal of the cartridge 150 may be indicated on the vaporizer device 100. For example, the removal of the cartridge 150 may be portrayed by the LEDs 136 with a predefined illumination of the LEDs 136. For example, the LEDs 136 being illuminated in a predefined color may be indicative of the removal of the cartridge 150. In some implementations, the predefined illumination to represent removal of the cartridge 150 may occur upon detection of the removal of the cartridge 150 and may be equal in duration to the timeout period, or may occur after the timeout period has elapsed for another predefined amount of time. The removal of the cartridge 150 may also be represented by predefined haptic feedback to indicate that the cartridge 150 has been removed from the vaporizer body 110. In some implementations, the predefined haptic feedback to represent removal of the cartridge 150 may occur upon detection of the removal of the cartridge 150 or after the timeout period has elapsed.

At 435, a determination is made as to whether the timeout period has elapsed. The removal of the cartridge 150 (as detected at 430), consistent with implementations of the current subject matter, may initiate the timeout period during which inserting the cartridge 150 back into the vaporizer body 110 results in the setpoint temperature incrementing to the next setpoint temperature in the sequence of setpoint temperatures. If the timeout period has elapsed, then the process ends at 440 (until the cartridge 150 may be reinserted at a later point in time). If however the timeout period has not elapsed, at 445 a determination is made as to whether the cartridge 150 is detected by the vaporizer body 110. If the cartridge 150 is not detected, the timeout period continues to be monitored until the timeout period ends.

If however the cartridge 150 is detected at 445 during the timeout period, at 450 the setpoint temperature is incremented to the next setpoint temperature in the sequence. For example, the setpoint temperature is incremented to the next setpoint temperature based on value of the setpoint temperatures or, if applicable, to the cartridge-associated setpoint temperature or the user-defined setpoint temperature.

At 455, the setpoint temperature may be indicated on the vaporizer device 100. For example, the detection of the cartridge 150 and/or the determination or identification of the setpoint temperature may be portrayed by the LEDs 136 with a predefined illumination of the LEDs 136. Additionally, the detection of the cartridge 150 may be represented by the LEDs 136 with a predefined cartridge detection illumination, which may include illumination and/or fading of the LEDs 136. Moreover, a predefined haptic feedback may also be provided to indicate insertion of the cartridge 150 and/or identification of the setpoint temperature. The haptic feedback may be a pulse or vibration provided by the haptics system 144 as described herein.

At 460, if the user device 305 is connected to the vaporizer device 100 and the app is running, an indication of the setpoint temperature may be provided on the user device 305.

Following 450 and 455, at which the setpoint temperature is incremented to the next setpoint temperature in the sequence of setpoint temperatures and the indication is provided on the vaporizer device 100, the process 400 continues back to 425 if cartridge removal is detected. Otherwise, if the cartridge 150 is not removed from the vaporizer body 110, the selected setpoint temperature is the temperature to which the heater 166 heats to produce vapor for consumption by the user.

FIG. 5A-FIG. 5F are example representations of temperature adjustment being portrayed by the display of the LEDs 136, according to implementations of the current subject matter.

As shown in representation 500 of FIG. 5A, the LEDs 136 of the vaporizer body 110 form an arrangement in which four individual petals (e.g., each petal is a single-color or multi-color/multi-channel LED) are arranged to form a circular type configuration, with each of the four individual petals positioned at or roughly at 90° angles from the adjacent petals. Such a configuration is purely exemplary and non-limiting to aspects of the current subject matter, and various other configurations may be utilized. For example, rather than four petals, four bars may be arranged in a horizontal or vertical line or other configuration. Rather than the petal shape or bar shape, any type of polygon may be used. Moreover, more than one shape may be used in a given configuration; for example, a combination of shapes may be used in a configuration of LEDs. Accordingly, various configurations of shapes including rectangles, squares, circles, ovals, etc. may be arranged in any manner.

As described herein, the setpoint temperatures, consistent with implementations of the current subject matter, are not limited to four specific setpoint temperatures, and/or the cartridge-associated setpoint temperature and/or the user-defined setpoint temperature. For example, the sequence of setpoint temperatures may include two, three, four, five, six, seven, eight, nine, ten, or more values. The number of LEDs need not correspond to the number of setpoint temperatures in the sequence. Rather, one LED may be used to represent one or more setpoint temperatures. For example, a particular color and/or illumination/fading sequence may be indicative of one setpoint temperature, while another color and/or illumination/fading sequence is indicative of another setpoint temperature. Such color or illumination/fading sequence may be applied to configurations with one or more LEDs.

In some implementations, one LED may be reserved to indicate the cartridge-associated setpoint temperature and/or the user-defined setpoint temperature. In some implementations, when the setpoint temperature in the sequence of setpoint temperatures is the cartridge-associated setpoint temperature and/or the user-defined setpoint temperature, a distinctive predefined illumination of the LEDs 136 may be used to signify the cartridge-associated setpoint temperature and/or the user-defined setpoint temperature. In the example in which the cartridge-associated setpoint temperature is placed in the sequence based on its value, and the example sequence is 270° C., 290° C. (e.g., the cartridge-associated setpoint temperature), 320° C., 370° C., and 420° C., one LED may illuminate to represent 270° C.; one LED may illuminate in a distinct color pattern to represent 290° C. (e.g., the cartridge-associated setpoint temperature); and two LEDs may illuminate to represent 320° C., three to represent 370° C., and four to represent 420° C.

In the exemplary configuration shown in FIG. 5A, a combination or pattern of illumination of the petals represents a given temperature (e.g., as shown, one petal illuminated is indicative of 270° C. (501), two petals illuminated is indicative of 320° C. (502), three petals illuminated is indicative of 370° C. (503), four petals illuminated is indicative of 420° C. (504), and a variation of the petals illuminated is indicative of the cartridge-associated or user-defined setpoint temperature (505)). It will be appreciated that the circular, four petal configuration provided in FIG. 5A allows for the user to easily discern the setpoint temperatures being displayed. Moreover, the circular configuration allows for the sequence of setpoint temperatures to be easily recognizable.

Consistent with implementations of the current subject matter, to easily identify the cartridge-associated setpoint temperature and/or the user-defined setpoint temperature in the sequence of setpoint temperatures, a unique illumination feature may be used. For example, a different color and/or a different effect (e.g., a twinkling, an ember effect, a brighter or darker illumination, and the like) may be used to signify the cartridge-associated setpoint temperature and/or the user-defined setpoint temperature. As the cartridge-associated setpoint temperature and/or the user-defined setpoint temperature is not limited to a particular value, they may be represented by illuminating the number of petals (with the unique illumination feature) that most closely corresponds to the cartridge-associated setpoint temperature and/or the user-defined setpoint temperature. For example, if the cartridge-associated setpoint temperature is 300° C., and the sequence of setpoint temperatures is 270° C. (one petal), 320° C. (two petals), 370° C. (three petals), and 420° C. (four petals), then the cartridge-associated setpoint temperature may be represented by one petal illuminated with a unique illumination feature.

Additionally, a unique haptic feedback may be provided. For example, a single pulse may be provided at each setpoint temperature in the sequence, and a longer pulse or a series of pulses may serve to signify the cartridge-associated setpoint temperature and/or the user-defined setpoint temperature.

Figure 5B:
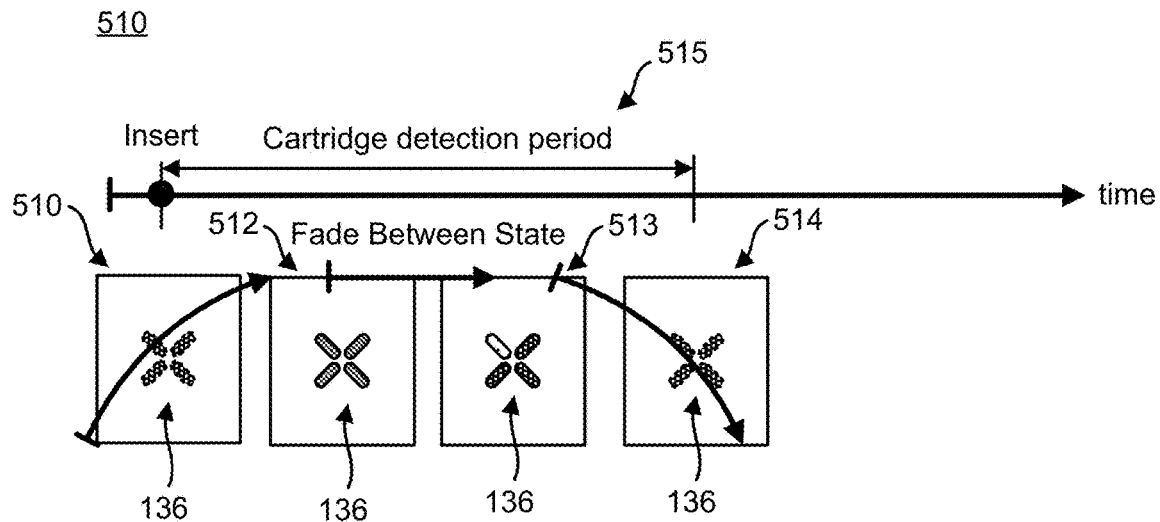

FIG. 5B includes a representation 510 illustrating the indication of the cartridge 150 inserted with the setpoint temperature equivalent to one petal. As shown, at 511, the LEDs 136 may be originally off (indicated by the gray color with dashed lines). Upon insertion of the cartridge 150 into the vaporizer body 110, at 512, the LEDs 136 may flash a certain color to provide a cartridge detection illumination. The cartridge detection illumination may fade to, at 513, one petal being illuminated to indicate the setpoint temperature. The one petal illumination may fade to, at 514, all of the LEDs 136 being off. A cartridge detection period 515 is defined, as shown, as the period of time from which the cartridge 150 is inserted in the vaporizer body 110 (511) until the one petal illumination fades to off (514). This sequence is just one example of the indication of the detection of the cartridge 150 and the setpoint temperature, and other sequences consistent with implementations of the current subject matter may be incorporated.

Figure 5C:
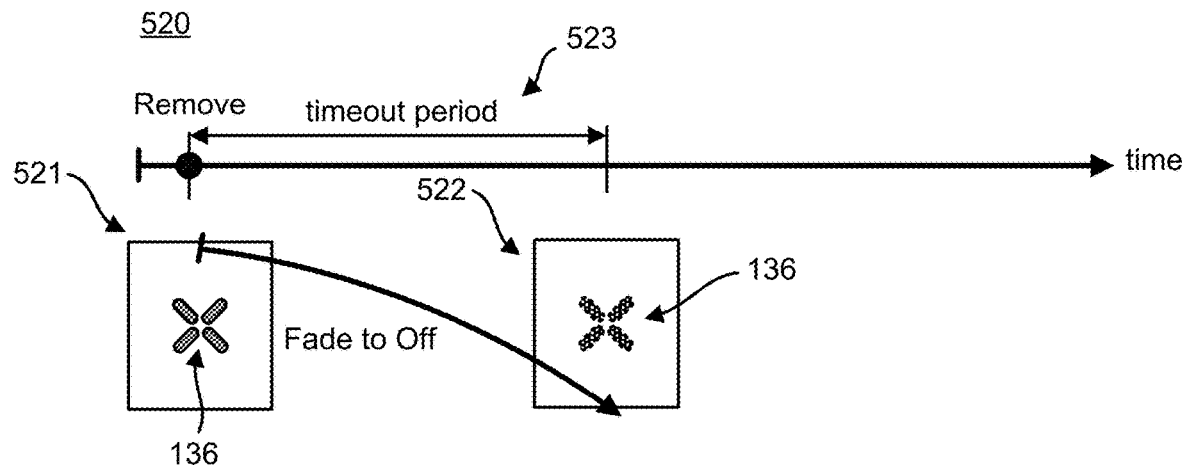

FIG. 5C includes a representation 520 illustrating the indication of the cartridge 150 being removed from the vaporizer body 110. As shown, at 521, the LEDs 136 may flash a certain color and then, at 522, fade to off. A timeout period 523 is shown as the period of time from which the cartridge 150 is removed from the vaporizer body (521) until the LEDs 136 fade off (522).

Figure 5D:
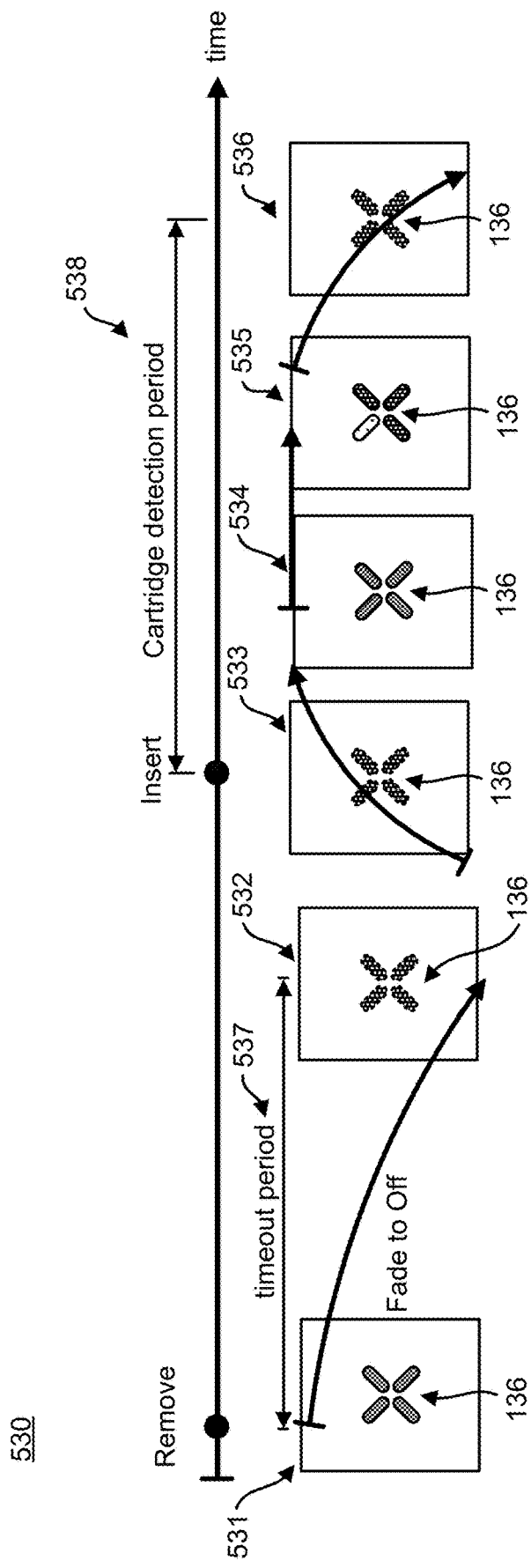

FIG. 5D includes a representation 530 illustrating a sequence of the cartridge 150 removed from the vaporizer body 110 and then inserted back into the vaporizer body 110. In particular, at 531, the LEDs 136 may flash a certain color and then, at 532, fade to off. A timeout period 537 is shown as the period of time from which the cartridge 150 is removed from the vaporizer body (531) until the LEDs 136 fade off (532). At 533, the LEDs 136 are off and the cartridge 150 is inserted. Upon insertion of the cartridge 150, at 534, the LEDs 136 may flash a certain color to provide a cartridge detection illumination. The cartridge detection illumination may fade to, at 535, one petal being illuminated to indicate the setpoint temperature. The one petal illumination may fade to, at 536, all of the LEDs 136 being off. A cartridge detection period 538 is defined, as shown, as the period of time from which the cartridge 150 is inserted in the vaporizer body 110 (533) until the one petal illumination fades off (536).

Figure 5E:
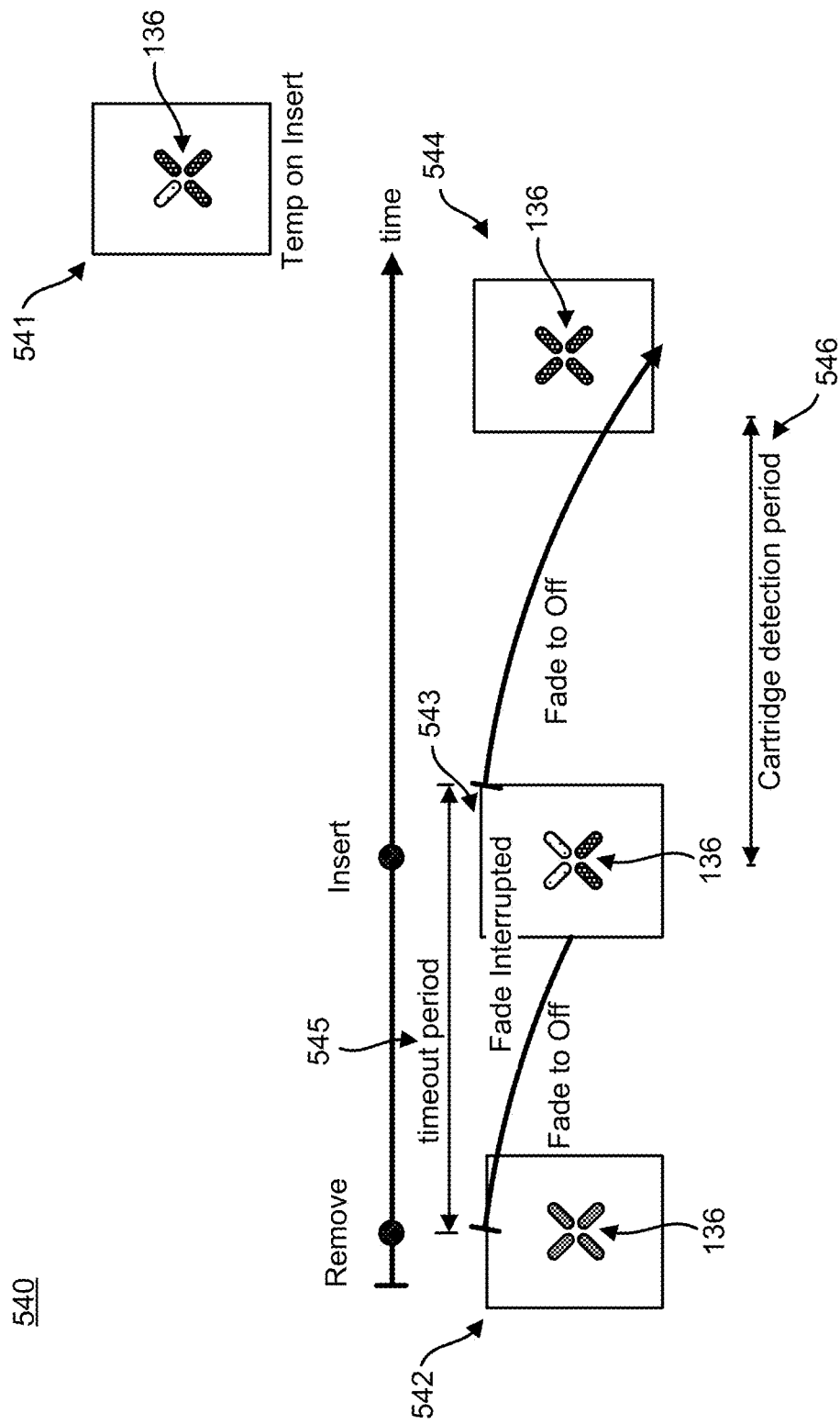

FIG. 5E includes a representation 540 illustrating the use of the timeout period to reinsert the cartridge 150 to increment the setpoint temperature to the next setpoint temperature in the sequence, consistent with implementations of the current subject matter. 541 illustrates the current setpoint temperature, represented by one petal illuminated. At 542, when the cartridge 150 is removed, the LEDs 136 flash a certain color and begin to fade off. At 543, before the fade off is complete (e.g., before a timeout period 545 has elapsed), the cartridge 150 is reinserted into the vaporizer body 110. This reinsertion during the timeout period causes the setpoint temperature of the cartridge 150 to increment to the next setpoint temperature in the sequence (as evidenced by the two petal illumination). After the cartridge 150 is inserted, with no other user controlled action, at 544, the illumination fades off. A cartridge detection period 546 is defined, as shown, as the period of time from which the cartridge 150 is inserted in the vaporizer body 110 (543), interrupting the timeout period 545, until the one petal illumination fades off (544).

Figure 5F:
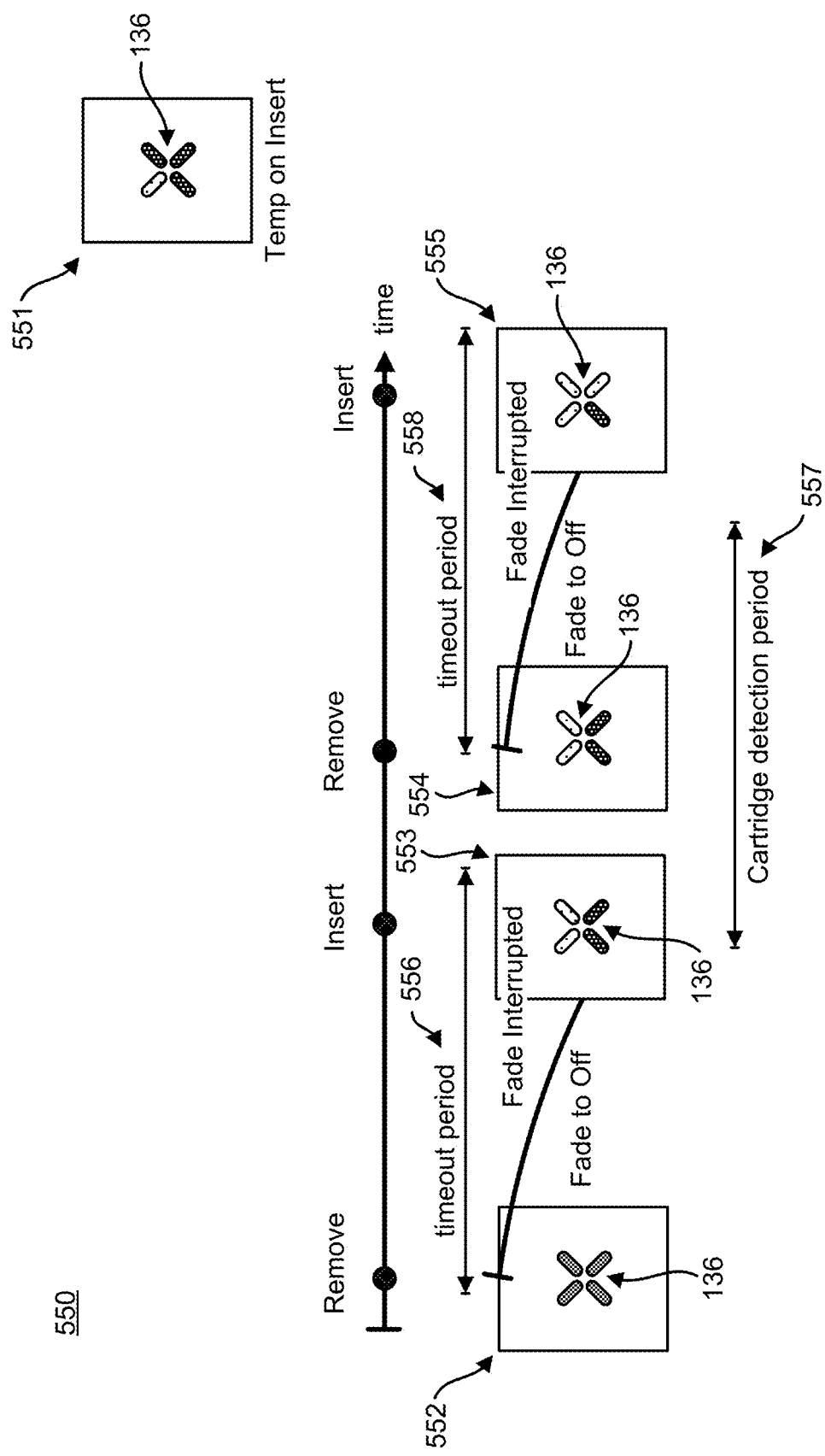

FIG. 5F includes a representation 550 in which in which the setpoint temperature is incremented from the setpoint temperature represented by one petal (at 551) to the temperature represented by three petals. 551 illustrates the current setpoint temperature, represented by one petal illuminated. At 552, when the cartridge 150 is removed, the LEDs 136 flash a certain color and begin to fade off. At 553, before the fade off is complete (e.g., before a timeout period 556 has elapsed), the cartridge 150 is reinserted into the vaporizer body 110. This reinsertion during the timeout period causes the setpoint temperature of the cartridge 150 to increment to the next setpoint temperature in the sequence (as evidenced by the two petal illumination). At 554, before the LEDs fade (and before completion of the cartridge detection period 557), the cartridge 150 is removed from the vaporizer body 110. The LEDs begin to fade off to represent the removal of the cartridge 150. At 555, before the fade off is complete (e.g., before a timeout period 558 has elapsed), the cartridge 150 is reinserted into the vaporizer body 110. This reinsertion during the timeout period causes the setpoint temperature of the cartridge 150 to increment to the next setpoint temperature in the sequence (as evidenced by the three petal illumination). This process may be repeated indefinitely until the user either removes and fails to reinsert the cartridge 150 or the user keeps the cartridge 150 in the vaporizer body 110. If the cartridge 150 remains in the vaporizer body 110, the last selected setpoint temperature is the temperature to which the heater 166 is heated for vaporization of the vaporizable material contained in the cartridge 150.

Figure 6:
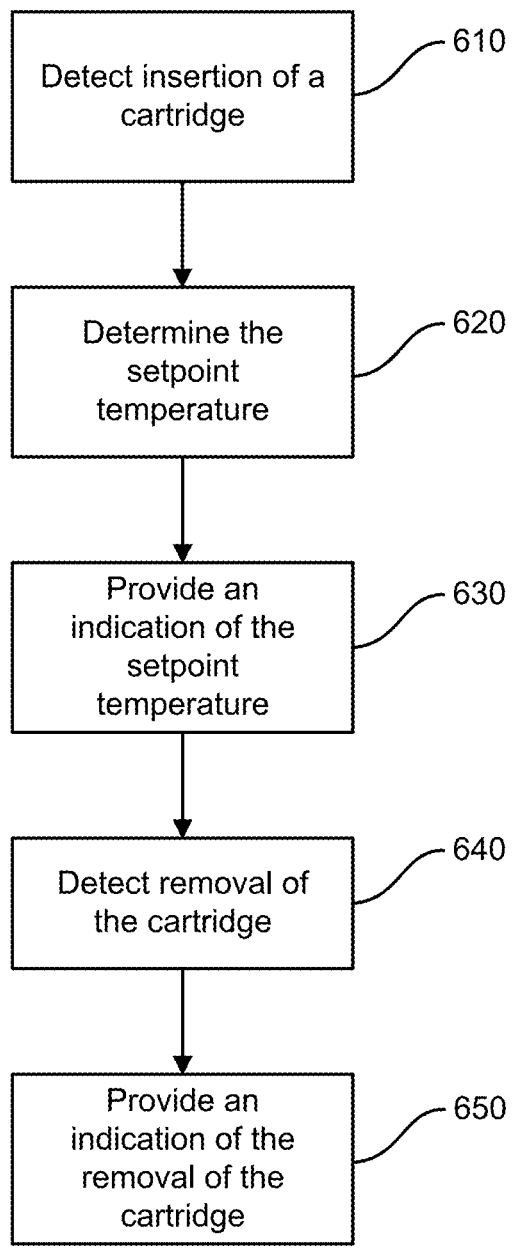
FIG. 6 shows a process flow chart illustrating features of a method consistent with some example implementations of the current subject matter.

With reference to FIG. 6, a process flow chart 600 illustrates features of temperature adjustment consistent with implementations of the current subject matter.

At 610, insertion of the cartridge 150 in the vaporizer body 110 is detected. For example, the cartridge detection circuitry 148 may detect that the cartridge 150 is inserted into the cartridge receptacle 114 due to a connection being established between the power pins 122*a,b* and the power pin receptacles 160*a,b*. The insertion of the cartridge 150 may initiate the temperature adjustment features of the current subject matter, allowing the user to increment through a sequence of setpoint temperatures, with a display on the vaporizer device 100 corresponding to the current setpoint temperature in the sequence of setpoint temperatures.

At 620, the setpoint temperature for vaporization by the heater 166 is determined. The setpoint temperature may be, for example, a default setpoint temperature, a cartridge-associated setpoint temperature, a vaporizer body-associated setpoint temperature, a previous setpoint temperature (e.g., carried over from previous use of the vaporizer device 100 and/or the cartridge 150), a user-defined setpoint temperature, or a next temperature in a sequence of setpoint temperatures.

The setpoint temperature may be determined by, for example, accessing data stored on a data tag such as the tag 164 of the cartridge 150, accessing memory such as the memory 146 of the vaporizer body 110, receiving the setpoint temperature from a user device such as the user device 305 in communication with the vaporizer body 110, receiving the setpoint temperature from a remote server such as the remote server 307, and/or receiving the setpoint temperature from another device, such as through a Bluetooth connection from another vaporizer device.

At 630, in response to the detection of the insertion of the cartridge 150 and the determination of the setpoint temperature, an indication of the setpoint temperature is provided on a display of the vaporizer body 110. For example, the detection of the cartridge 150 and the determination or identification of the setpoint temperature may be portrayed by the LEDs 136 with a predefined illumination and/or fading of the LEDs 136. The display may include a plurality of LEDs, such as the LEDs 136, and a predefined pattern of illumination of the LEDs my correspond to a certain setpoint temperature. The indication of the setpoint temperature may include the LEDs illuminated in the predefined pattern of illumination that corresponds to the setpoint temperature.

At 640, removal of the cartridge 150 from the vaporizer body 110 may be detected. For example, the cartridge detection circuitry 148 may detect a disconnection between the power pins 122*a,b* and the power pin receptacles 160*a,b*.

Consistent with implementations of the current subject matter, the removal of the cartridge 150 may initiate a timeout period, during which reinsertion of the cartridge 150 into the vaporizer body 110 acts to increment the setpoint temperature to the next setpoint temperature in a sequence of setpoint temperatures. If the cartridge 150 is reinserted prior to the timeout period elapsing, the setpoint temperature is incremented to the next setpoint temperature, and an indication of the next setpoint temperature is provided on the display of the vaporizer body 110. For example, a predefined pattern of illumination corresponding to the value of the next setpoint temperature may be provided via the LEDs 136 on the vaporizer body 110.

According to aspects of the current subject matter, the sequence of setpoint temperatures defines a series of setpoint temperatures through which the vaporizer device 100 may be incremented. The sequence of setpoint temperatures may include a cartridge-associated setpoint temperature and a user-defined setpoint temperature. The cartridge-associated setpoint temperature and/or the user-defined setpoint temperature may be positioned within the sequence of setpoint temperatures based on a value of the cartridge-associated setpoint temperature and/or a value of the user-defined setpoint temperature, or may be positioned as a last setpoint temperature within the sequence of setpoint temperatures, or may be positioned in other portions of the sequence of setpoint temperatures.

At 650, in response to the detection of the removal of the cartridge 150, an indication of the removal of the cartridge 150 may be provided on the display of the vaporizer body 110. In some implementations, the indication of the removal of the cartridge 150 may include the plurality of LEDs, such as the LEDs 136, being illuminated in a predefined cartridge removal pattern to indicate to the user that the timeout period has begun. For example, the predefined cartridge removal pattern may include the LEDs 136 illuminating and fading, where the end of the timeout period is represented by the LEDs 136 fading to off.

The temperature adjustment aspects of the current subject matter provide a user with a controlled, intuitive, and simple method to adjust the setpoint temperature of the vaporizer device 100. The temperature adjustment aspects provide for quickly incrementing through a sequence of setpoint temperatures, allowing the user to select the desired setpoint temperature for use with the vaporizer device 100, while also providing a display that indicates the setpoint temperatures. A timeout period is provided, and may be defined, for incrementing through the sequence of setpoint temperatures. Moreover, a cartridge-associated setpoint temperature and/or a user-defined setpoint temperature may be included in the sequence of setpoint temperatures, allowing a user to utilize of cartridge-specific recommendations and/or user preferences with respect to setpoint temperature.

In some examples, the vaporizable material may include a viscous liquid such as, for example a cannabis oil. In some variations, the cannabis oil comprises between 0.3% and 100% cannabis oil extract. The viscous oil may include a carrier for improving vapor formation, such as, for example, propylene glycol, glycerol, medium chain triglycerides (MCT) including lauric acid, capric acid, caprylic acid, caproic acid, etc., at between 0.01% and 25% (e.g., between 0.1% and 22%, between 1% and 20%, between 1% and 15%, and/or the like). In some variations the vapor-forming carrier is 1,3-Propanediol. A cannabis oil may include a cannabinoid or cannabinoids (natural and/or synthetic), and/or a terpene or terpenes derived from organic materials such as for example fruits and flowers. For example, any of the vaporizable materials described herein may include one or more (e.g., a mixture of) cannabinoid including one or more of: CBG (Cannabigerol), CBC (Cannabichromene), CBL (Cannabicyclol), CBV (Cannabivarin), THCV (Tetrahydrocannabivarin), CBDV (Cannabidivarin), CBCV (Cannabichromevarin), CBGV (Cannabigerovarin), CBGM (Cannabigerol Monomethyl Ether), Tetrahydrocannabinol, Cannabidiol (CBD), Cannabinol (CBN), Tetrahydrocannabinolic Acid (THCA), Cannabidioloc Acid (CBDA), Tetrahydrocannabivarinic Acid (THCVA), one or more Endocannabinoids (e.g., anandamide, 2-Arachidonoylglycerol, 2-Arachidonyl glyceryl ether, N-Arachidonoyl dopamine, Virodhamine, Lysophosphatidylinositol), and/or a synthetic cannabinoids such as, for example, one or more of: JWH-018, JWH-073, CP-55940, Dimethylheptylpyran, HU-210, HU-331, SR144528, WIN 55,212-2, JWH-133, Levonantradol (Nantrodolum), and AM-2201. The oil vaporization material may include one or more terpene, such as, for example, Hemiterpenes, Monoterpenes (e.g., geraniol, terpineol, limonene, myrcene, linalool, pinene, Iridoids), Sesquiterpenes (e.g., humulene, farnesenes, farnesol), Diterpenes (e.g., cafestol, kahweol, cembrene and taxadiene), Sesterterpenes, (e.g., geranylfarnesol), Triterpenes (e.g., squalene), Sesquarterpenes (e.g., ferrugicadiol and tetraprenylcurcumene), Tetraterpenes (lycopene, gamma-carotene, alpha- and beta-carotenes), Polyterpenes, and Norisoprenoids. For example, an oil vaporization material as described herein may include between 0.3-100% cannabinoids (e.g., 0.5-98%, 10-95%, 20-92%, 30-90%, 40-80%, 50-75%, 60-80%, etc.), 0-40% terpenes (e.g., 1-30%, 10-30%, 10-20%, etc.), and 0-25% carrier (e.g., medium chain triglycerides (MCT)).

In any of the oil vaporizable materials described herein (including in particular, the cannabinoid-based vaporizable materials), the viscosity may be within a predetermined range. The range may be between, at room temperature (23° C.) about 30 cP (centipoise) and 115 kcP (kilocentipoise), between 30 cP and 200 kcP, although higher viscosities and/or lower viscosities may be implemented as well. For example, the viscosity may be between 40 cP and 113 kcP at room temperature. Outside of this range, the vaporizable material may fail in some instances to wick appropriately to form a vapor as described herein. In particular, it is typically desired that the oil may be made sufficiently thin to both permit wicking at a rate that is useful with the apparatuses described herein, while also limiting leaking (e.g., viscosities below that of ~30 cP at room temperature might result in problems with leaking).

Although the disclosure, including the figures, described herein may described and/or exemplify these different variations separately, it should be understood that all or some, or components of them, may be combined.

Although various illustrative embodiments are described above, any of a number of changes may be made to various embodiments. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the claims.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. References to a structure or feature that is disposed "adjacent" another feature may have portions that overlap or underlie the adjacent feature.

Terminology used herein is for the purpose of describing particular embodiments only and is not intended to be limiting. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as, for example, "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings provided herein.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

As used herein in the specification and claims, including as used in the examples and unless otherwise expressly specified, all numbers may be read as if prefaced by the word "about" or "approximately," even if the term does not expressly appear. The phrase "about" "or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, are possible.

In the descriptions above and in the claims, phrases such as, for example, "at least one of" or "one or more of" may occur followed by a conjunctive list of elements or features. The term "and/or" may also occur in a list of two or more elements or features. Unless otherwise implicitly or explicitly contradicted by the context in which it used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." Use of the term "based on," above and in the claims is intended to mean, "based at least in part on," such that an unrecited feature or element is also permissible.

One or more aspects or features of the subject matter described herein can be realized in digital electronic circuitry, integrated circuitry, specially designed application specific integrated circuits (ASICs), field programmable gate arrays (FPGAs) computer hardware, firmware, software, and/or combinations thereof. These various aspects or features can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device. The programmable system or computing system may include clients and servers. A client and server are generally remote from each other and typically interact through a communication network.

The relationship of client and server arises by virtue of computer programs running on the respective computers and having a client-server relationship to each other.

These computer programs, which can also be referred to as programs, software, software applications, applications, components, or code, include machine instructions for a programmable processor, and can be implemented in a high-level procedural language, an object-oriented programming language, a functional programming language, a logical programming language, and/or in assembly/machine language. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium can store such machine instructions non-transitorily, such as for example as would a non-transient solid-state memory or a magnetic hard drive or any equivalent storage medium. The machine-readable medium can alternatively or additionally store such machine instructions in a transient manner, such as for example as would a processor cache or other random access memory associated with one or more physical processor cores.

To provide for interaction with a user, one or more aspects or features of the subject matter described herein can be implemented on a computer having a display device, such as for example a cathode ray tube (CRT) or a liquid crystal display (LCD) or a light emitting diode (LED) monitor for displaying information to the user and a keyboard and a pointing device, such as for example a mouse or a trackball, by which the user may provide input to the computer. Other kinds of devices can be used to provide for interaction with a user as well. For example, feedback provided to the user can be any form of sensory feedback, such as for example visual feedback, auditory feedback, or tactile feedback; and input from the user may be received in any form, including, but not limited to, acoustic, speech, or tactile input. Other possible input devices include, but are not limited to, touch screens or other touch-sensitive devices such as single or multi-point resistive or capacitive trackpads, voice recognition hardware and software, optical scanners, optical pointers, digital image capture devices and associated interpretation software, and the like.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A method, comprising:
   detecting insertion of a cartridge in a vaporizer body, the cartridge comprising a heating element configured to deliver heat to a vaporizable material contained in the cartridge, wherein the heat causes vaporization of the vaporizable material;
   determining, in response to detecting insertion of the cartridge, a first setpoint temperature for the heating element;
   providing, on a display of the vaporizer body, an indication of the first setpoint temperature;
   performing a temperature incrementing process, including:
      detecting a first removal of the cartridge from the vaporizer body, wherein the temperature incrementing process begins solely based on the first removal of the cartridge from the vaporizer body;
      providing, on the display of the vaporizer body and in response to detecting the first removal of the cartridge, an indication of the first removal of the cartridge;
      detecting, during a first timeout period and following the first removal of the cartridge, a first reinsertion of the cartridge in the vaporizer body;
      incrementing, in response to detecting the first reinsertion of the cartridge during the first timeout period, the first setpoint temperature to a second setpoint temperature in a sequence of setpoint temperatures; and
      providing, on the display of the vaporizer body, an indication of the second setpoint temperature; and
      activating the heating element to reach the second setpoint temperature for vaporization of the vaporizable material.

2. The method of claim 1, wherein the first setpoint temperature comprises a default setpoint temperature, a cartridge-associated setpoint temperature, a vaporizer body-associated setpoint temperature, a previous setpoint temperature, or a user-defined setpoint temperature.

3. The method of claim 1, wherein determining the first setpoint temperature comprises at least one of accessing data stored on a data tag of the cartridge, accessing a memory component in the vaporizer body, and receiving the first setpoint temperature from a device in communication with the vaporizer body.

4. The method of claim 1, wherein the display comprises a plurality of light-emitting diodes, wherein the indication of the first setpoint temperature comprises a first predefined pattern of illumination of the plurality of light-emitting diodes, wherein the indication of the second setpoint temperature comprises a second predefined pattern of illumination of the plurality of light-emitting diodes.

5. The method of claim 1, wherein the display comprises a plurality of light-emitting diodes, wherein the indication of the first removal of the cartridge comprises the plurality of light-emitting diodes illuminated in a predefined cartridge removal pattern.

6. The method of claim 5, wherein a length of time of the predefined cartridge removal pattern equals the first timeout period.

7. The method of claim 1, wherein the indication of the next setpoint temperature interrupts the indication of the first removal of the cartridge.

8. The method of claim 1, wherein the sequence of setpoint temperatures defines a series of temperatures including at least the setpoint temperature and the next setpoint temperature.

9. The method of claim 8, wherein the sequence of setpoint temperatures further comprises at least one of a cartridge-associated setpoint temperature and a user-defined setpoint temperature.

10. The method of claim 9, wherein the at least one of the cartridge-associated setpoint temperature and the user-defined setpoint temperature is positioned within the sequence of setpoint temperatures based on at least one of a value of the cartridge-associated setpoint temperature and a value of the user-defined setpoint temperature, or is positioned as a last setpoint temperature within the sequence of setpoint temperatures.

11. The method of claim 1, further comprising:
providing, on the display of the vaporizer body and in response to detecting insertion of the cartridge, an indication of the insertion of the cartridge, wherein the indication of the insertion of cartridge precedes the indication of the first setpoint temperature.

12. The method of claim 1, further comprising:
detecting a second removal of the cartridge from the vaporizer body;
providing, on the display of the vaporizer body and in response to detecting the second removal of the cartridge, an indication of the second removal of the cartridge;
detecting, during a second timeout period and following the second removal of the cartridge, reinsertion of the cartridge in the vaporizer body;
incrementing, in response to detecting reinsertion of the cartridge during the second timeout period, the next setpoint temperature to a third setpoint temperature in the sequence of setpoint temperature;
providing, on the display of the vaporizer body, an indication of the third setpoint temperature; and
activating the heating element to reach the third setpoint temperature for vaporization of the vaporizable material.

13. The method of claim 1, further comprising: wherein the temperature incrementing process further includes:
initiating, upon detecting the first removal of the cartridge, the first timeout period, wherein the detecting the first removal indicates a start of a first remove and insert operation, wherein the first remove and insert operation comprises the first removal of the cartridge and the first reinsertion of the cartridge in the vaporizer body, wherein the first reinsertion of the cartridge is an initial first reinsertion of the cartridge following the first removal of the cartridge, wherein the first remove and insert operation is configured to cause the first setpoint temperature to be incremented to the second setpoint temperature, wherein the second setpoint temperature directly follows the first setpoint temperature in a defined order within the sequence of setpoint temperatures, and wherein the detecting the first reinsertion indicates an end of the first remove and insert operation; and
wherein the method further includes performing a second temperature incrementing process including:
detecting a second removal of the cartridge from the vaporizer body, wherein the second removal of the cartridge is an initial removal of the cartridge following the first removal of the cartridge, wherein the detecting the second removal indicates a start of a second remove and insert operation, wherein the second remove and insert operation comprises the second removal of the cartridge and a second reinsertion of the cartridge in the vaporizer body, wherein the second reinsertion of the cartridge is an initial second reinsertion of the cartridge following the second removal of the cartridge, wherein the second remove and insert operation is configured to cause the second setpoint temperature to be incremented to a third setpoint temperature, and wherein the third setpoint temperature directly follows the second setpoint temperature in the defined order within the sequence of setpoint temperatures;
initiating, upon detecting the second removal of the cartridge, a second timeout period separate from the first timeout period;
providing, on the display of the vaporizer body and in response to detecting the second removal of the cartridge, an indication of the second removal of the cartridge;
detecting, during the second timeout period, the second reinsertion of the cartridge in the vaporizer body, wherein the detecting the second reinsertion indicates an end of the second remove and insert operation;
incrementing, in response to detecting the second reinsertion of the cartridge during the second timeout period, the second setpoint temperature to the third setpoint temperature; and
providing, on the display of the vaporizer body, an indication of the third setpoint temperature; and
activating the heating element to reach the third setpoint temperature for vaporization of the vaporizable material.

14. The method of claim 13, further comprising:
performing a third temperature incrementing process including:
detecting a third removal of the cartridge from the vaporizer body, wherein the third removal of the cartridge is an initial removal of the cartridge following the second removal of the cartridge, wherein the detecting the third removal indicates a start of a third remove and insert operation, wherein the third remove and insert operation comprises the third removal of the cartridge and a third reinsertion of the cartridge in the vaporizer body, wherein the third reinsertion of the cartridge is an initial third reinsertion of the cartridge following the third removal of the cartridge, wherein the third remove and insert operation is configured to cause the third setpoint temperature to be incremented to a fourth setpoint temperature, and wherein the fourth setpoint temperature directly follows the third setpoint temperature in the defined order within the sequence of setpoint temperatures;
initiating, upon detecting the third removal of the cartridge, a third timeout period separate from the first timeout period and the second timeout period;
providing, on the display of the vaporizer body and in response to detecting the third removal of the cartridge, an indication of the third removal of the cartridge;
detecting, during the third timeout period, the third reinsertion of the cartridge in the vaporizer body, wherein the detecting the third reinsertion indicates an end of the third remove and insert operation;

incrementing, in response to detecting the third reinsertion of the cartridge during the third timeout period, the third setpoint temperature to the fourth setpoint temperature; and providing, on the display of the vaporizer body, an indication of the fourth setpoint temperature; and wherein the method further includes activating the heating element to reach the fourth setpoint temperature for vaporization of the vaporizable material.

15. The method of claim 1, wherein the temperature incrementing process of claim 1, wherein incrementing the first setpoint temperature to the second setpoint temperature is solely based on the detecting of the first removal of the cartridge from the vaporizer body and the detection of the first reinsertion of the cartridge during the first timeout period following removal of the cartridge.

16. A vaporizer device, comprising:

at least one data processor; and at least one memory storing instructions which, when executed by the at least one data processor, cause operations comprising:

detecting insertion of a cartridge in a vaporizer body, the cartridge comprising a heating element configured to deliver heat to a vaporizable material contained in the cartridge, wherein the heat causes vaporization of the vaporizable material;

determining, in response to detecting insertion of the cartridge, a setpoint temperature for the heating element;

providing, on a display of the vaporizer body, an indication of the setpoint temperature;

performing a temperature incrementing process, including:

detecting removal of the cartridge from the vaporizer body, wherein the temperature incrementing process begins solely based on the removal of the cartridge from the vaporizer body;

providing, on the display of the vaporizer body and in response to detecting removal of the cartridge, an indication of the removal of the cartridge;

detecting, during a timeout period and following removal of the cartridge, reinsertion of the cartridge in the vaporizer body;

incrementing, in response to detecting reinsertion of the cartridge during the timeout period, the setpoint temperature to a next setpoint temperature in a sequence of setpoint temperatures; and providing, on the display of the vaporizer body, an indication of the next setpoint temperature; and activating the heating element to reach the next setpoint temperature for vaporization of the vaporizable material.

17. The vaporizer device of claim 16, wherein the setpoint temperature comprises a default setpoint temperature, a cartridge-associated setpoint temperature, a vaporizer body-associated setpoint temperature, a previous setpoint temperature, or a user-defined setpoint temperature.

18. The vaporizer device of claim 16, wherein determining the setpoint temperature comprises at least one of accessing data stored on a data tag of the cartridge, accessing a memory component in the vaporizer body, and receiving the setpoint temperature from a device in communication with the vaporizer body.

19. The vaporizer device of claim 16, wherein the display comprises a plurality of light-emitting diodes, wherein the indication of the setpoint temperature comprises a first predefined pattern of illumination of the plurality of light-emitting diodes, wherein the indication of the next setpoint temperature comprises a second predefined pattern of illumination of the plurality of light-emitting diodes.

20. The vaporizer device of claim 16, wherein the display comprises a plurality of light-emitting diodes, wherein the indication of the removal of the cartridge comprises the plurality of light-emitting diodes illuminated in a predefined cartridge removal pattern.

21. The vaporizer device of claim 20, wherein a length of time of the predefined cartridge removal pattern equals the timeout period.

22. The vaporizer device of claim 16, wherein the indication of the next setpoint temperature interrupts the indication of the removal of the cartridge.

23. The vaporizer device of claim 16, wherein the sequence of setpoint temperatures defines a series of temperatures including at least the setpoint temperature and the next setpoint temperature.

24. The vaporizer device of claim 23, wherein the sequence of setpoint temperatures further comprises at least one of a cartridge-associated setpoint temperature and a user-defined setpoint temperature.

25. The vaporizer device of claim 24, wherein the at least one of the cartridge-associated setpoint temperature and the user-defined setpoint temperature is positioned within the sequence of setpoint temperatures based on at least one of a value of the cartridge-associated setpoint temperature and a value of the user-defined setpoint temperature, or is positioned as a last setpoint temperature within the sequence of setpoint temperatures.

26. The vaporizer device of claim 16, wherein the at least one memory storing instructions, when executed by the at least one data processor, cause operations further comprising:

providing, on the display of the vaporizer body and in response to detecting insertion of the cartridge, an indication of the insertion of the cartridge, wherein the indication of the insertion of cartridge precedes the indication of the setpoint temperature.

27. The vaporizer device of claim 16, wherein the at least one memory storing instructions, when executed by the at least one data processor, cause operations further comprising:

detecting a second removal of the cartridge from the vaporizer body;

providing, on the display of the vaporizer body and in response to detecting the second removal of the cartridge, an indication of the second removal of the cartridge;

detecting, during a second timeout period and following the second removal of the cartridge, reinsertion of the cartridge in the vaporizer body;

incrementing, in response to detecting reinsertion of the cartridge during the second timeout period, the next setpoint temperature to a third setpoint temperature in the sequence of setpoint temperatures;

providing, on the display of the vaporizer body, an indication of the third setpoint temperature; and activating the heating element to reach the third setpoint temperature for vaporization of the vaporizable material.

28. A non-transitory computer readable medium storing instructions, which when executed by at least one data processor, result in operations comprising:

detecting insertion of a cartridge in a vaporizer body, the cartridge comprising a heating element configured to deliver heat to a vaporizable material contained in the cartridge, wherein the heat causes vaporization of the vaporizable material;

determining, in response to detecting insertion of the cartridge, a setpoint temperature for the heating element;

providing, on a display of the vaporizer body, an indication of the setpoint temperature;

performing a temperature incrementing process, including:

detecting removal of the cartridge from the vaporizer body, wherein the temperature incrementing process begins solely based on the removal of the cartridge from the vaporizer body;

providing, on the display of the vaporizer body and in response to detecting removal of the cartridge, an indication of the removal of the cartridge;

detecting, during a timeout period and following removal of the cartridge, reinsertion of the cartridge in the vaporizer body;

incrementing, in response to detecting reinsertion of the cartridge during the timeout period, the setpoint temperature to a next setpoint temperature in a sequence of setpoint temperatures; and providing, on the display of the vaporizer body, an indication of the next setpoint temperature; and activating the heating element to reach the next setpoint temperature for vaporization of the vaporizable material.

\* \* \* \* \*